United States Patent
Iwane

(10) Patent No.: US 12,262,875 B2
(45) Date of Patent: Apr. 1, 2025

(54) ENDOSCOPE SYSTEM

(71) Applicant: FUJIFILM Corporation, Tokyo (JP)

(72) Inventor: Kosuke Iwane, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 403 days.

(21) Appl. No.: 17/741,027

(22) Filed: May 10, 2022

(65) Prior Publication Data

US 2022/0265129 A1 Aug. 25, 2022

Related U.S. Application Data

(63) Continuation of application No. PCT/JP2020/038508, filed on Oct. 12, 2020.

(30) Foreign Application Priority Data

Nov. 12, 2019 (JP) .................................. 2019-204913

(51) Int. Cl.
*A61B 1/06* (2006.01)
*A61B 1/00* (2006.01)
*A61B 1/045* (2006.01)

(52) U.S. Cl.
CPC ...... *A61B 1/0655* (2022.02); *A61B 1/000095* (2022.02); *A61B 1/00045* (2013.01); *A61B 1/045* (2013.01); *A61B 1/00066* (2013.01)

(58) Field of Classification Search
CPC ............ A61B 1/0655; A61B 1/000095; A61B 1/00045; A61B 1/045; A61B 1/00066; A61B 1/0653
See application file for complete search history.

(56) References Cited

U.S. PATENT DOCUMENTS

2009/0023991 A1* 1/2009 Gono .................. G01J 3/32
600/109
2011/0228064 A1* 9/2011 Sasaki ............ A61B 1/00188
348/E7.085

(Continued)

FOREIGN PATENT DOCUMENTS

| WO | 2013/031701 A1 | 3/2013 |
| WO | 2019/093355 A1 | 5/2019 |
| WO | 2019/163471 A1 | 8/2019 |

OTHER PUBLICATIONS

International Search Report issued in PCT/JP2020/038508; mailed Nov. 24, 2020.

(Continued)

*Primary Examiner* — Nasim N Nirjhar
(74) *Attorney, Agent, or Firm* — Studebaker Brackett PLLC

(57) ABSTRACT

An endoscope system includes a processor. The processor has a plurality of observation modes including main observation modes and a sub-observation mode, performs main switching processing for switching the plurality of main observation modes in a predetermined order according to a first operation and performs sub-switching processing for performing switching between a specific main observation mode and the sub-observation mode according to a second operation different from the first operation, and controls a display aspect in each observation mode. An observation image displayed in the specific main observation mode and an observation image displayed in the sub-observation mode have the same base color tone.

8 Claims, 24 Drawing Sheets

(56) References Cited

U.S. PATENT DOCUMENTS

| | | |
|---|---|---|
| 2013/0286175 A1 | 10/2013 | Hashimoto et al. |
| 2017/0319057 A1 | 11/2017 | Inglese et al. |
| 2019/0282135 A1* | 9/2019 | Ito .......................... A61B 1/044 |
| 2020/0260942 A1 | 8/2020 | Kubo |
| 2021/0382559 A1* | 12/2021 | Segev ..................... G06F 3/013 |

OTHER PUBLICATIONS

Written Opinion of the International Searching Authority issued in PCT/JP2020/038508; mailed Nov. 24, 2020.

An Office Action; "Notice of Reasons for Refusal," mailed by the Japanese Patent Office on Nov. 15, 2022, which corresponds to Japanese Patent Application No. 2021-555949 and is related to U.S. Appl. No. 17/741,027; with English language translation.

\* cited by examiner

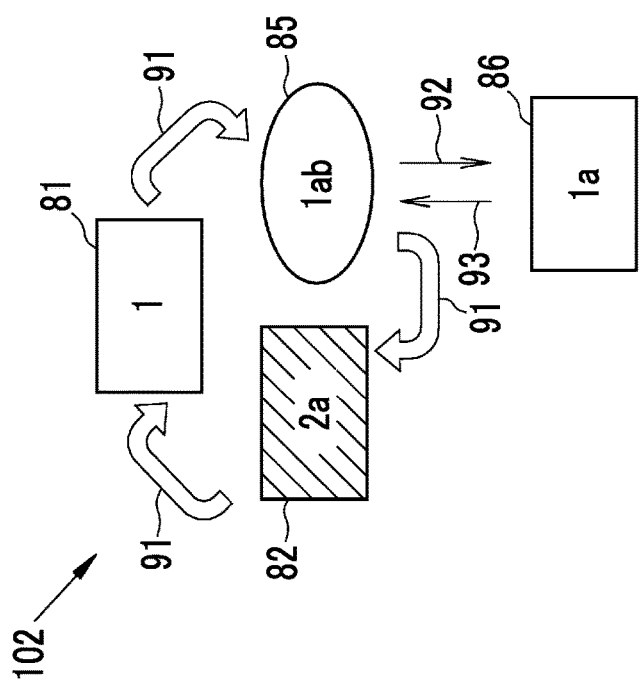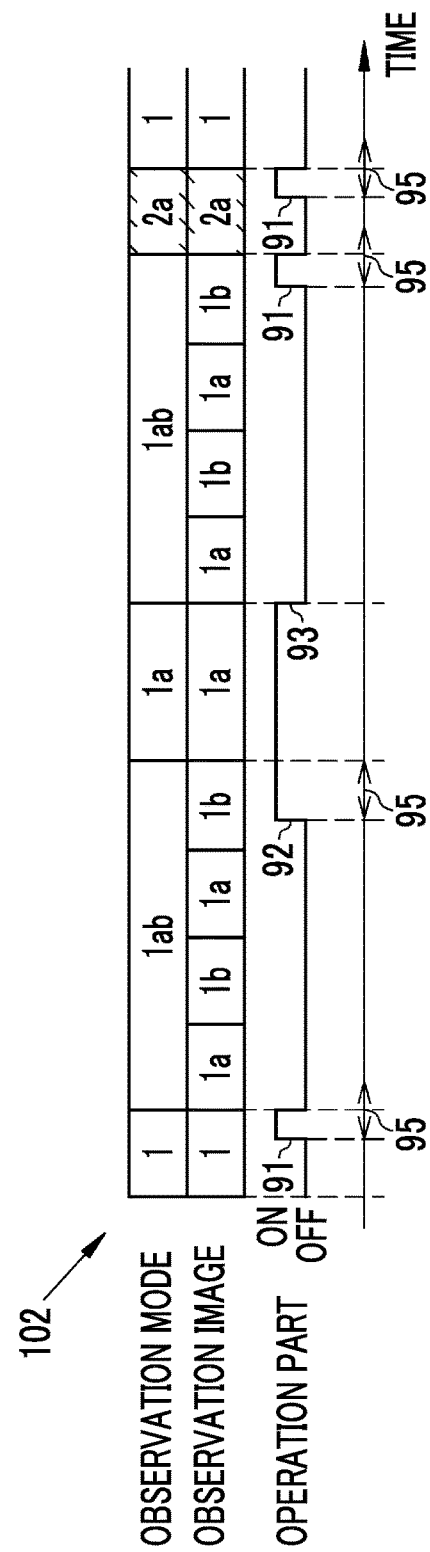

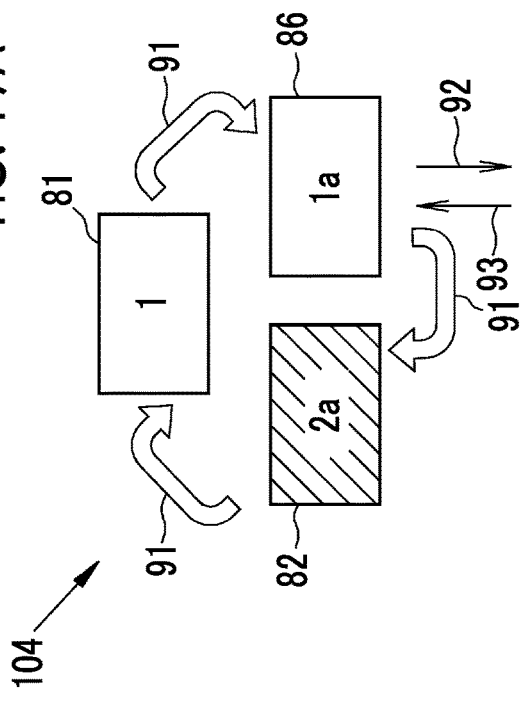
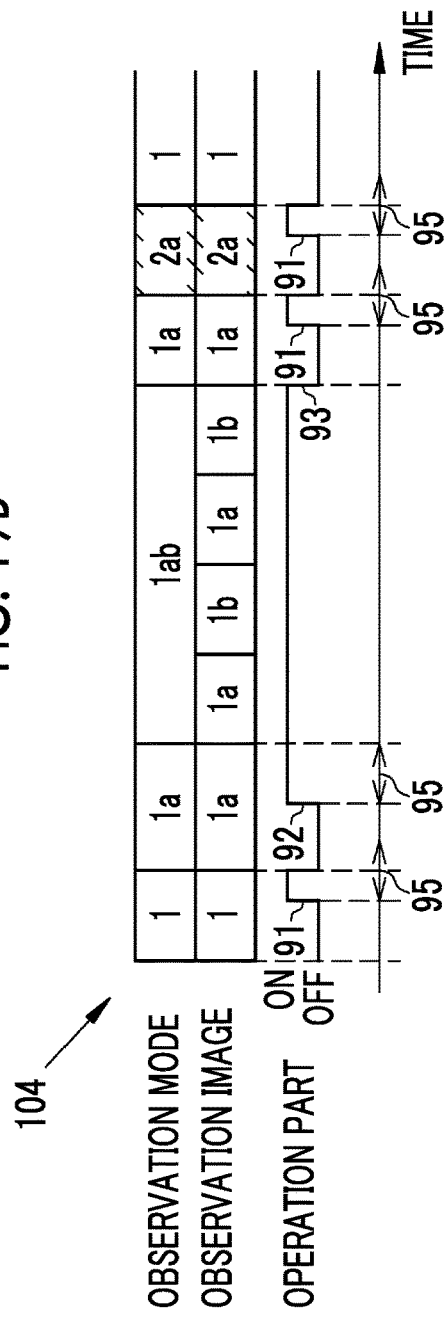

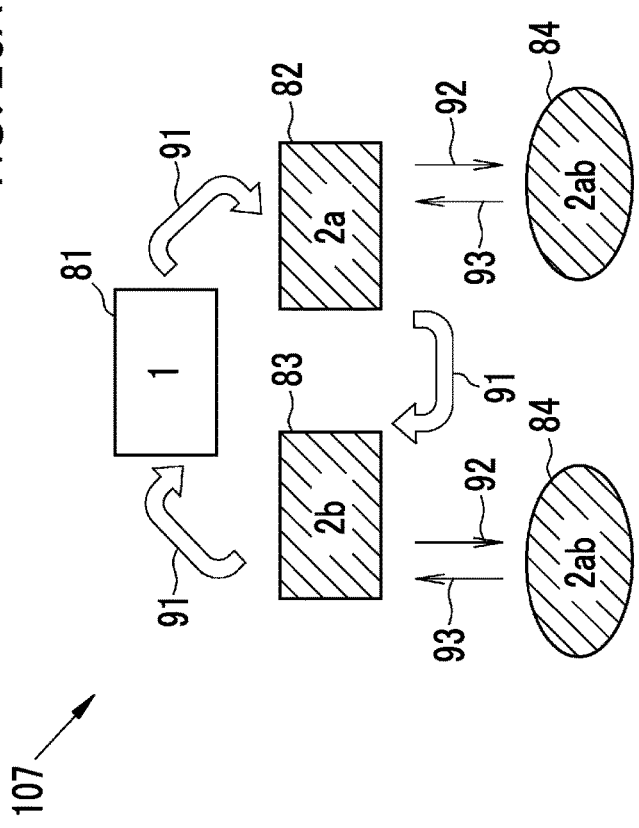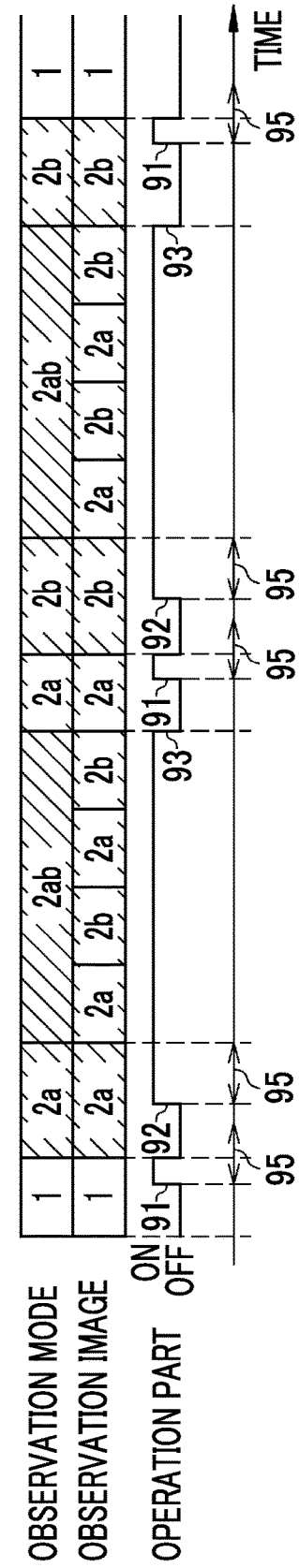

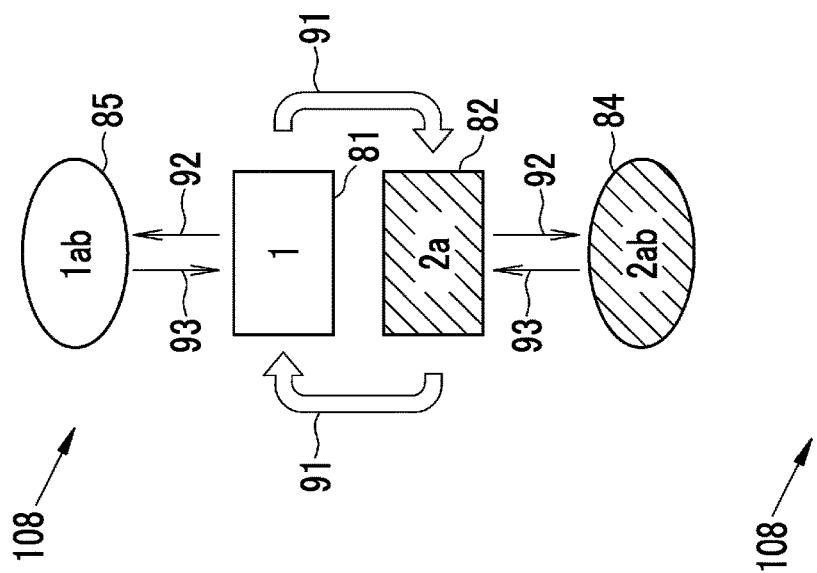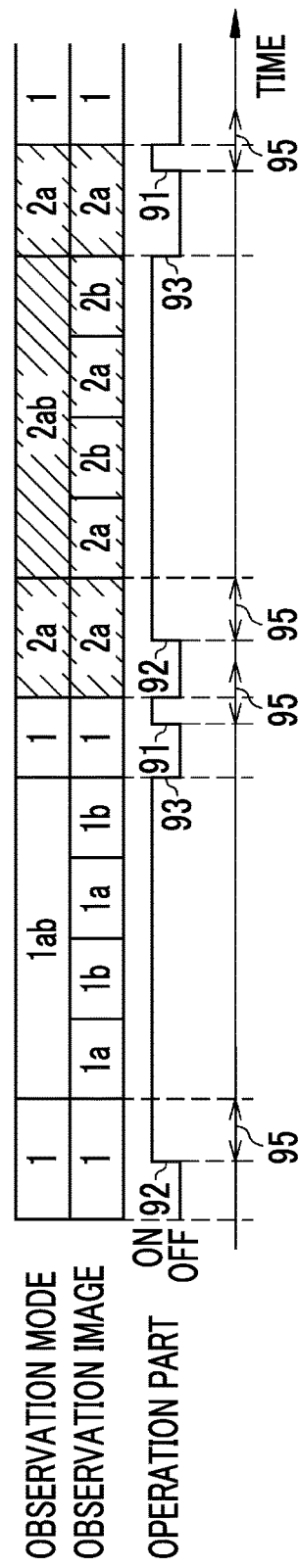

ENDOSCOPE SYSTEM

CROSS-REFERENCE TO RELATED APPLICATIONS

This application is a Continuation of PCT International Application No. PCT/JP2020/038508 filed on 12 Oct. 2020, which claims priority under 35 U.S.C § 119(a) to Japanese Patent Application No. 2019-204913 filed on 12 Nov. 2019. The above application is hereby expressly incorporated by reference, in its entirety, into the present application.

BACKGROUND OF THE INVENTION

1. Field of the Invention

The present invention relates to an endoscope system having a plurality of observation modes.

2. Description of the Related Art

In a medical field, a diagnosis has been generally made using an endoscope system that includes a light source device, an endoscope, and a processor device. An endoscope system, which picks up the image of an object to be observed using white light as illumination light and has not only a normal observation mode but also a special observation mode, has been used in recent years. In the normal observation mode, an observable image, which has a natural color tone, of the object to be observed is acquired and displayed. In the special observation mode, a study is made on the wavelength of illumination light to be applied to an object to be observed or signal processing, such as spectral estimation processing, is performed on image signals obtained from the image pickup of an object to be observed to display the minute change of a mucosal surface layer, an observation image in which specific tissue or structures, such as blood vessels or ducts, are enhanced, and the like. An observer allows lesions to be screened or diagnosed by switching the plurality of observation modes and displaying and comparing different types of images. Accordingly, the screening or diagnosis of the lesions is made more reliable. For example, in a case where images, which are obtained in a plurality of special observation modes and of which color tones are changed, are compared with each other, it may be possible to identify a cancer and other portion of a lesion area, such as the stomach, on a display screen by using colors.

The switching of observation modes including the normal observation mode, the special observation mode, and the like is generally performed by a push button type automatic return switch (momentary switch) attached to an endoscope. Whenever the push button is pressed once by the observer, the observation mode is shifted in a specific order. As a result, an image to be displayed on the display is also shifted. In this way, the observer can switch images, which are to be displayed in the plurality of observation modes, in a specific order even during the operation of the endoscope. Accordingly, it is possible to compare different types of images.

WO2019/163471A discloses an endoscope system that has a plurality of observation modes and can be conveniently shifted to a different observation mode and returned to the original observation mode by a single switch operation. Accordingly, the endoscope system can be shifted between three types of observation modes by a single operation.

SUMMARY OF THE INVENTION

In a case where observation modes are switched and displayed images are compared with each other in the endoscope system having the plurality of observation modes, information useful for screening, a diagnosis, or the like is obtained. In order to make advanced and more accurate screening, diagnosis, or the like, it may be preferable to compare a plurality of observation images selected from observation images obtained in many observation modes depending on the purpose of observation and the like. Further, it is preferable that different portions, feature portions, or the like are likely to be recognized in the observation images to be compared with each other. Accordingly, an endoscope system, which can flexibly and conveniently perform the switching of a plurality of observation modes including related observation modes, is desired.

An object of the present invention is to provide an endoscope system that has a plurality of observation modes and can flexibly and conveniently perform the switching of the plurality of observation modes including related observation modes.

An endoscope system according to an aspect of the present invention comprises a processor. The processor displays an observation image on a display in a specific display aspect in each observation mode in a case where the processor has a plurality of observation modes including a plurality of main observation modes and a sub-observation mode, and performs main switching processing for switching the plurality of main observation modes in a predetermined order according to a first operation and performs sub-switching processing for performing switching between a specific main observation mode of the plurality of main observation modes and the sub-observation mode according to a second operation different from the first operation. The specific display aspect includes an automatic switching display aspect in which a plurality of the observation images are automatically switched and displayed on the display and a continuous display aspect in which the observation image is continuously displayed on the display, and the observation image displayed in the specific main observation mode and the observation image displayed in the sub-observation mode have the same base color tone.

It is preferable that the observation images are displayed on the display in the automatic switching display aspect in the specific main observation mode and the observation image is displayed on the display in the continuous display aspect in the sub-observation mode.

It is preferable that the specific main observation mode is a first ab-observation mode in which two images, that is, a first a-image and a first b-image having a first base color tone are displayed on the display in the automatic switching display aspect and the sub-observation mode is any one of a first a-observation mode in which the first a-image having the first base color tone is displayed on the display in the continuous display aspect or a first b-observation mode in which the first b-image having the first base color tone is displayed on the display in the continuous display aspect.

It is preferable that the specific main observation mode is a second ab-observation mode in which two images, that is, a second a-image and a second b-image having a second base color tone are displayed on the display in the automatic switching display aspect and the sub-observation mode is any one of a second a-observation mode in which the second a-image having the second base color tone is displayed on the display in the continuous display aspect or a second b-observation mode in which the second b-image having the second base color tone is displayed on the display in the continuous display aspect.

It is preferable that the observation image is displayed on the display in the continuous display aspect in the specific main observation mode and the observation images are displayed on the display in the automatic switching display aspect in the sub-observation mode.

It is preferable that the specific main observation mode is any one of a first a-observation mode in which a first a-image having a first base color tone is displayed on the display in the continuous display aspect or a first b-observation mode in which a first b-image having the first base color tone is displayed on the display in the continuous display aspect and the sub-observation mode is a first ab-observation mode in which two images, that is, the first a-image and the first b-image having the first base color tone are displayed on the display in the automatic switching display aspect.

It is preferable that the specific main observation mode is a first observation mode in which a first image having a first base color tone is displayed on the display in the continuous display aspect and the sub-observation mode is a first ab-observation mode in which two images, that is, a first a-image and a first b-image having the first base color tone are displayed on the display in the automatic switching display aspect.

It is preferable that the specific main observation mode is any one of a second a-observation mode in which a second a-image having a second base color tone is displayed on the display in the continuous display aspect or a second b-observation mode in which a second b-image having the second base color tone is displayed on the display in the continuous display aspect and the sub-observation mode is a second ab-observation mode in which two images, that is, the second a-image and the second b-image having the second base color tone are displayed on the display in the automatic switching display aspect.

It is preferable that a plurality of the specific main observation modes are provided.

It is preferable that the specific main observation mode includes at least one specific main observation mode in which an image having a first base color tone is displayed on the display and at least one specific main observation mode in which an image having a second base color tone is displayed on the display.

It is preferable that the endoscope system further comprises a specific operation part that is used to perform both the first operation and the second operation.

It is preferable that the first operation is a single press operation for pressing the specific operation part for a time less than a certain time and the second operation is a long press operation for pressing the specific operation part for a time equal to or longer than the certain time or a long press release operation for releasing the pressing of the specific operation part.

It is preferable that the endoscope system further comprises a first operation part that is used to perform the first operation and a second operation part that is used to perform the second operation.

The endoscope system of the aspect of the present invention has a plurality of observation modes and can flexibly and conveniently perform the switching of the plurality of observation modes including related observation modes.

BRIEF DESCRIPTION OF THE DRAWINGS

FIG. 16A is a diagram illustrating a second pattern of the flow of an observation mode and FIG. 16B is a diagram illustrating a relationship between an operation in the second pattern and the observation mode.

FIG. 19A is a diagram illustrating a fourth pattern of the flow of an observation mode and FIG. 19B is a diagram illustrating a relationship between an operation in the fourth pattern and the observation mode.

FIG. 23A is a diagram illustrating a seventh pattern of the flow of an observation mode and FIG. 23B is a diagram illustrating a relationship between an operation in the seventh pattern and the observation mode.

FIG. 24A is a diagram illustrating an eighth pattern of the flow of an observation mode and FIG. 24B is a diagram illustrating a relationship between an operation in the eighth pattern and the observation mode.

DESCRIPTION OF THE PREFERRED EMBODIMENTS

Figure 1:
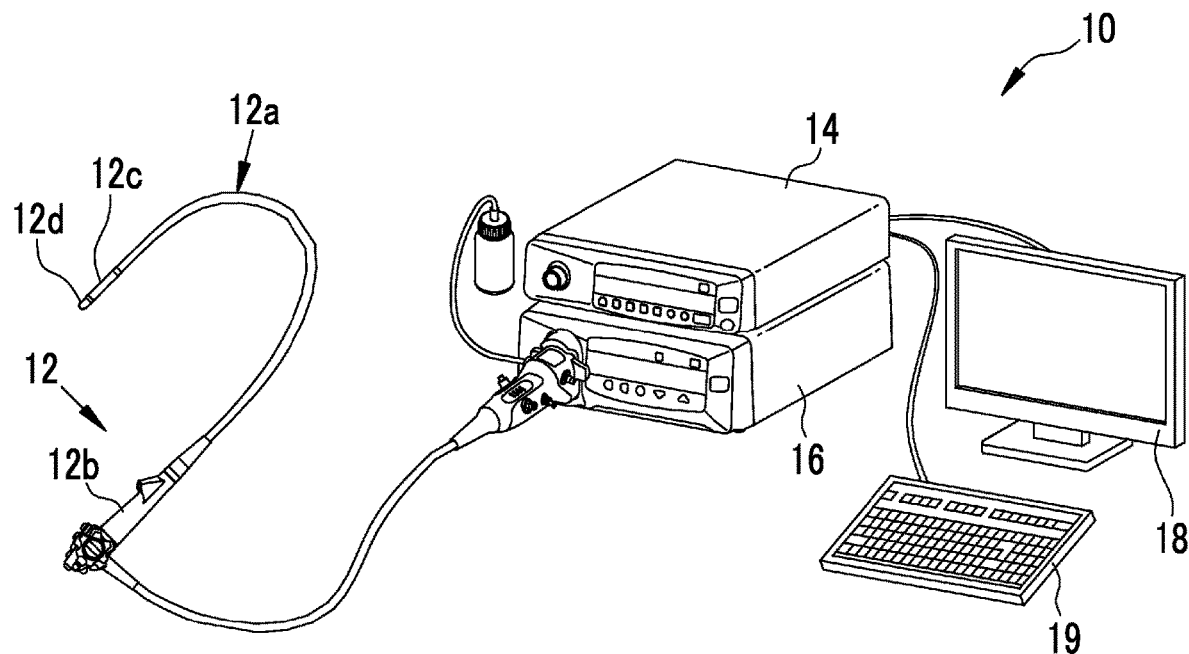
FIG. 1 is a diagram showing the appearance of an endoscope system.

In FIG. 1, an endoscope system 10 includes an endoscope 12, a light source device 14, a processor device 16, a display 18, and a console 19. The endoscope 12 is optically connected to the light source device 14, and is electrically connected to the processor device 16. The endoscope 12 includes an insertion part 12a that is to be inserted into the body of an object to be observed, an operation part 12b that is provided at the proximal end portion of the insertion part 12a, and a bendable part 12c and a distal end part 12d that are provided on the distal end side of the insertion part 12a. In a case where angle knobs 12e (see FIG. 2) of the operation part 12b are operated, the bendable part 12c is operated to be bent. As the bendable part 12c is operated to be bent, the distal end part 12d is made to face in a desired direction.

Figure 2:
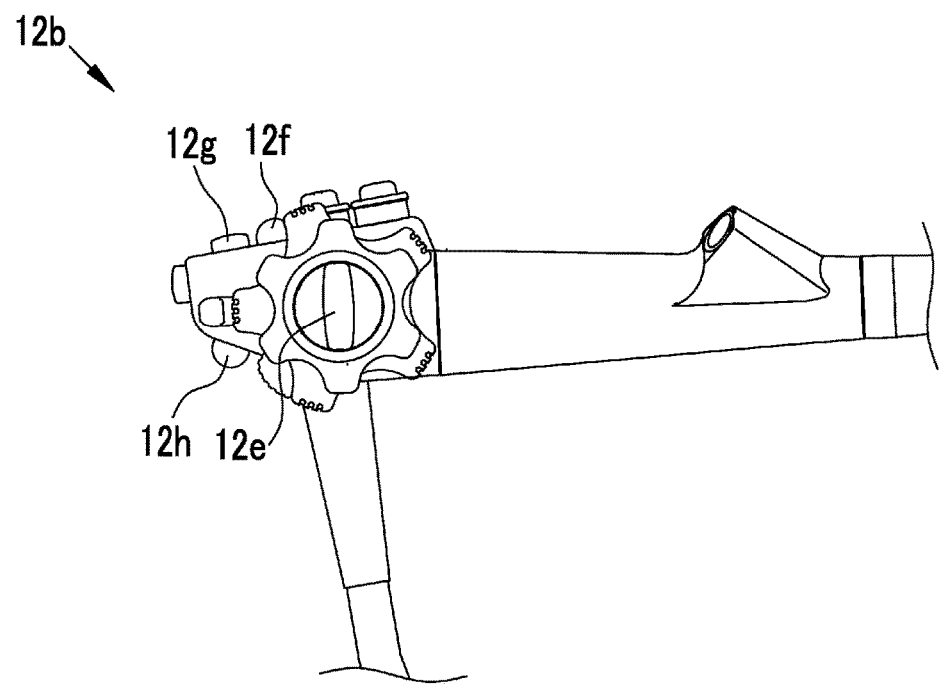
FIG. 2 is a diagram showing the appearance of an operation part of an endoscope.

As shown in FIG. 2, the operation part 12b is provided with a mode changeover switch 12g that is used for an operation for switching an observation mode and a zoom operation part 12h that is used for an instruction to increase/reduce the size of an endoscopic image, in addition to the angle knobs 12e. An auxiliary mode changeover switch 12f may be used for an operation for switching an observation mode. An operation using the console 19, a foot switch (not shown), or the like other than a scope switch, such as the mode changeover switch 12g or the auxiliary mode changeover switch 12f, may be performed as an operation for switching an observation mode.

The endoscope system 10 has a plurality of observation modes. In each observation mode included in the plurality of observation modes, a specific type of observation image is displayed on the display 18. Each observation mode is switched using the mode changeover switch 12g, the auxiliary mode changeover switch 12f, or the like by a first operation and a second operation different from the first operation. Switching processing in the first operation is different from that in the second operation. Accordingly, in a case where an observation is made in a certain observation mode, an observation mode after being switched in a case where the first operation is performed may be different from an observation mode after being switched in a case where the second operation is performed. Switching processing will be described later.

Each observation mode forms an observation mode group depending on the base color tone of a specific type of observation image to be displayed. The endoscope system 10 has a first observation mode group and a second observation mode group. That is, all the respective observation images displayed in a plurality of observation modes included in the first observation mode group have the same base color tone, and this base color tone is referred to as a first base color tone. Further, all the respective observation images displayed in a plurality of observation modes included in the second observation mode group have the same base color tone, and this base color tone is referred to as a second base color tone. A base color tone is a color tone that serves as a base in an observation image. In a case where observation images have the same base color tone even though being different from each other, the color tones of the observation images are not significantly different from each other as a whole at the time of comparison of the observation images and it is easy to recognize a different between portions other than the base color tone. A base color tone is, for example, a color tone of which a ratio of the area occupied in an observation image is high.

In the endoscope system 10, the first observation mode group includes a first observation mode, a first a-observation mode, a first b-observation mode, and a first ab-observation mode. In the first observation mode, the first a-observation mode, and the first b-observation mode, an observation image is displayed on the display 18 in a continuous display aspect in which an observation image is continuously displayed. The first ab-observation mode is an observation mode in which the first a-observation mode and the first b-observation mode are automatically switched. In the first ab-observation mode, observation images are displayed on the display 18 in an automatic switching display aspect in which observation images are automatically switched and displayed on the display 18. In all these observation modes, observation images have the first base color tone as the base color tones thereof. Accordingly, the base color tone of each of all observation images in the first observation mode, the first a-observation mode, the first b-observation mode, and the first ab-observation mode is the first base color tone, and all the observation images have the same base color tone. In an observation mode classified into the first observation mode group, an observation image having a natural color tone is displayed on the display 18.

Further, the second observation mode group includes a second a-observation mode, a second b-observation mode, and a second ab-observation mode. In the second a-observation mode and the second b-observation mode, an observation image is displayed on the display 18 in a continuous display aspect in which an observation image is continuously displayed. The second ab-observation mode is an observation mode in which the second a-observation mode and the second b-observation mode are automatically switched. In the second ab-observation mode, observation images are displayed on the display 18 in an automatic switching display aspect in which observation images are automatically switched and displayed on the display 18. In all these observation modes, observation images have the second base color tone as the base color tones thereof. Accordingly, the base color tone of each of all observation images in the second a-observation mode, the second b-observation mode, and the second ab-observation mode is the second base color tone, and all the observation images have the same base color tone. In an observation mode classified into the second observation mode group, an observation image in which a specific structure is enhanced is displayed on the display 18.

The processor device 16 is electrically connected to the display 18 and the console 19. The display 18 is an example of a display unit that outputs and displays an observation image, information attached to the observation image, and the like. The console 19 functions as a user interface that receives an input operation, such as function settings. An external recording unit (not shown) in which images, image information, and the like are recorded may be connected to the processor device 16.

Figure 3:
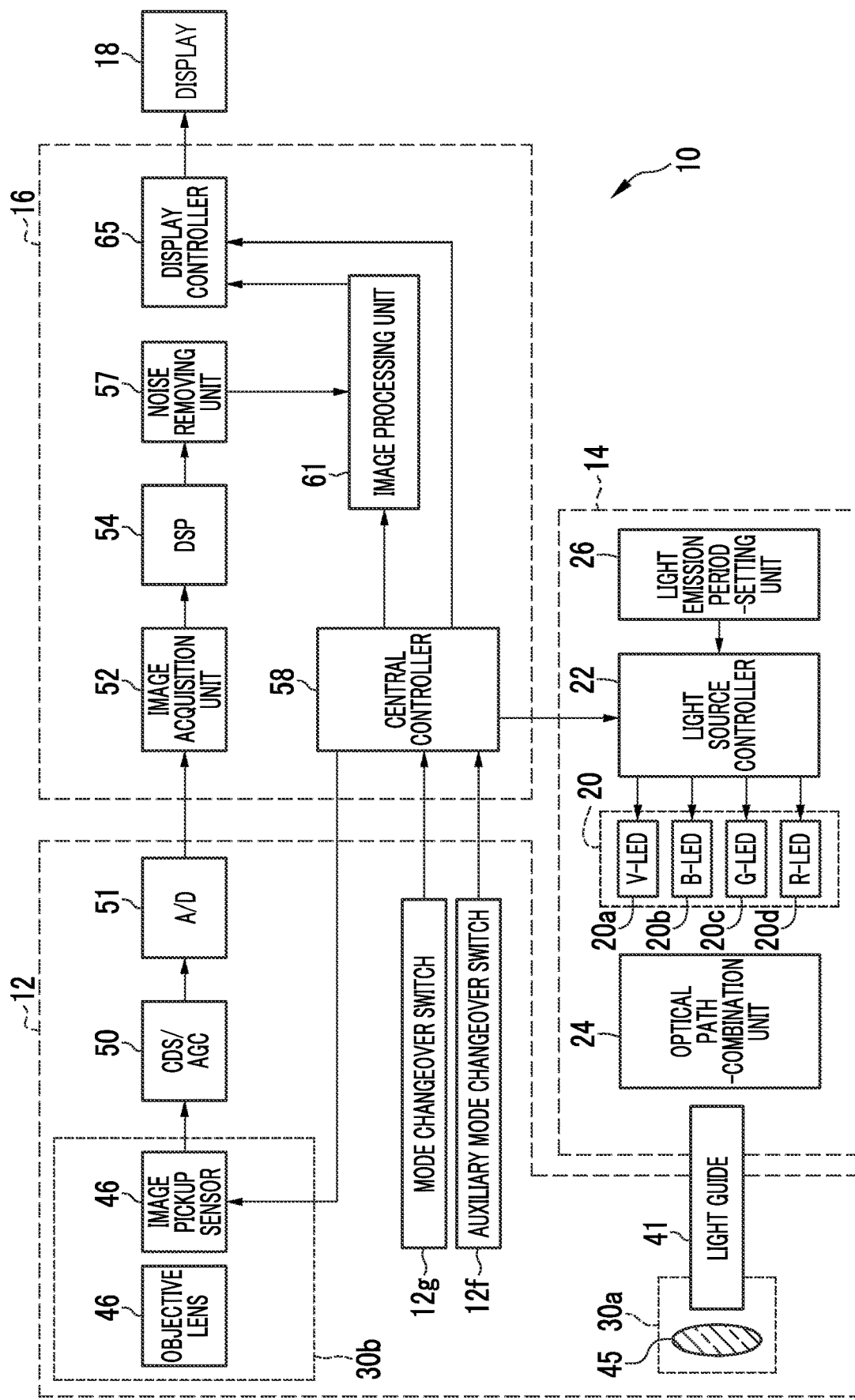
FIG. 3 is a block diagram showing the functions of the endoscope system.

As shown in FIG. 3, the light source device 14 includes a light source unit 20, a light source controller 22, an optical path-combination unit 24, and a light emission period-setting unit 26. The light source unit 20 includes four color LEDs 20a to 20d, that is, a violet light emitting diode (V-LED) 20a, a blue light emitting diode (B-LED) 20b, a green light emitting diode (G-LED) 20c, and a red light emitting diode (R-LED) 20d. The light source controller 22 controls the drive of the LEDs 20a to 20d. The optical path-combination unit 24 combines the optical paths of four kinds of color light that are emitted from the four color LEDs 20a to 20d. The inside of an object to be examined is irradiated with the pieces of light, which are combined by the optical path-combination unit 24, through a light guide 41 inserted into the insertion part 12a and an illumination lens 45. A laser diode (LD) may be used instead of the LED. The light emission period-setting unit 26 sets the light emission periods of a plurality of pieces of illumination light.

Figure 4:
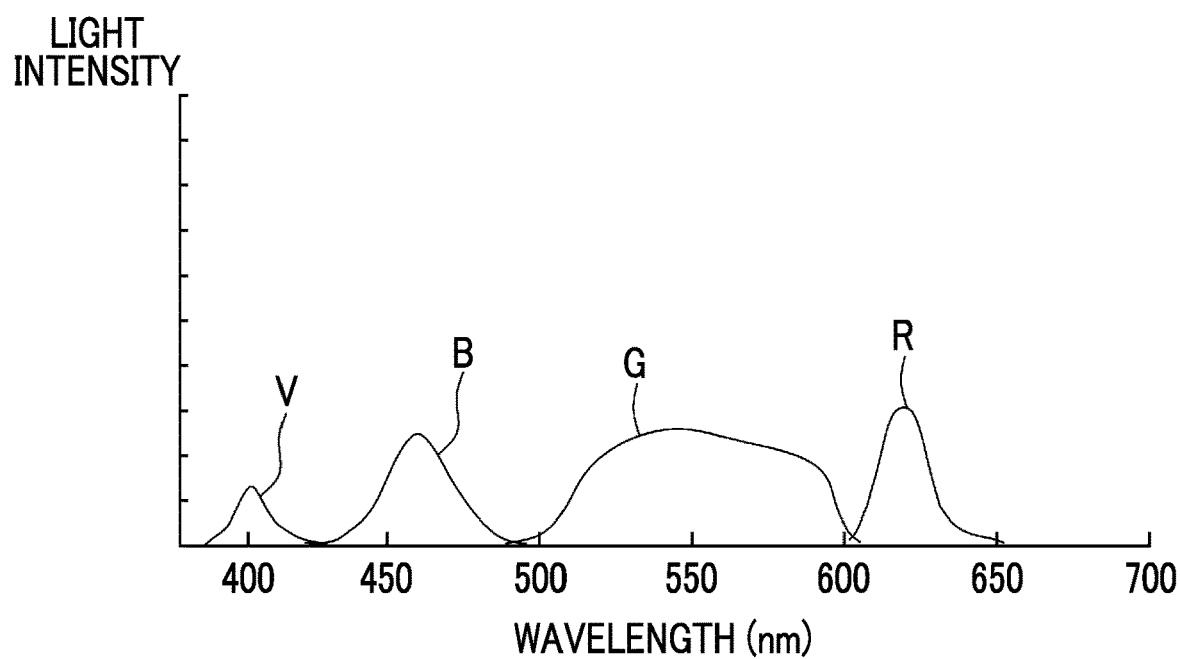
FIG. 4 is a graph showing the spectrum of normal light.

As shown in FIG. 4, the V-LED 20a generates violet light V of which the central wavelength is in the range of 405±10 nm and the wavelength range is in the range of 380 to 420 nm. The B-LED 20b generates blue light B of which the central wavelength is in the range of 460±10 nm and the wavelength range is in the range of 420 to 500 nm. The G-LED 20c generates green light G of which the wavelength range is in the range of 480 to 600 nm. The R-LED 20d generates red light R of which the central wavelength is in the range of 620 to 630 nm and the wavelength range is in the range of 600 to 650 nm.

The light source controller 22 controls the V-LED 20a, the B-LED 20b, the G-LED 20c, and the R-LED 20d. Further, in a case where the endoscope system 10 is set to the first observation mode, the light source controller 22 controls the respective LEDs 20a to 20d so that normal light of which a light intensity ratio between violet light V, blue light B, green light G, and red light R is Vc:Bc:Gc:Rc is emitted.

Figure 5:
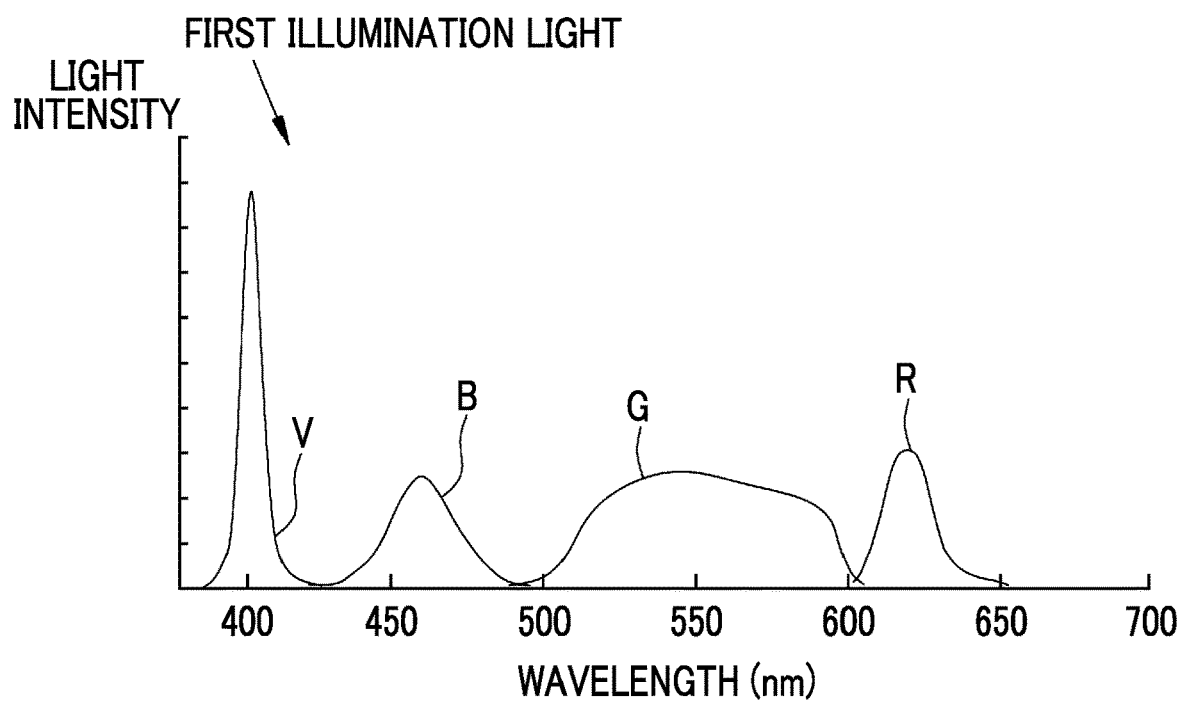
FIG. 5 is a graph showing the spectrum of first illumination light.

Furthermore, in a case where the endoscope system 10 is set to the first a-observation mode, the light source controller 22 controls the respective LEDs 20a to 20d so that first illumination light of which a light intensity ratio between violet light V, blue light B, green light G, and red light R is Vs1:Bs1:Gs1:Rs1 is emitted. The light intensity ratio Vs1:Bs1:Gs1:Rs1 corresponds to the light amount condition of the first illumination light. It is preferable that the first illumination light enhances superficial blood vessels. For this purpose, it is preferable that the light intensity of violet light V of the first illumination light is set to be higher than the light intensity of blue light B thereof. For example, as shown in FIG. 5, a ratio of the light intensity Vs1 of violet light V to the light intensity Bs1 of blue light B is set to "4:1".

In this specification, a light intensity ratio includes a case where the ratio of at least one semiconductor light source is 0 (zero). Accordingly, a light intensity ratio includes a case where any one or two of the respective semiconductor light sources are not turned on. For example, even though only one semiconductor light source is turned on and the other three semiconductor light sources are not turned on as in a case where a light intensity ratio between violet light V, blue light B, green light G, and red light R is 1:0:0:0, it is regarded that the light source unit 20 has a light intensity ratio.

Figure 6:
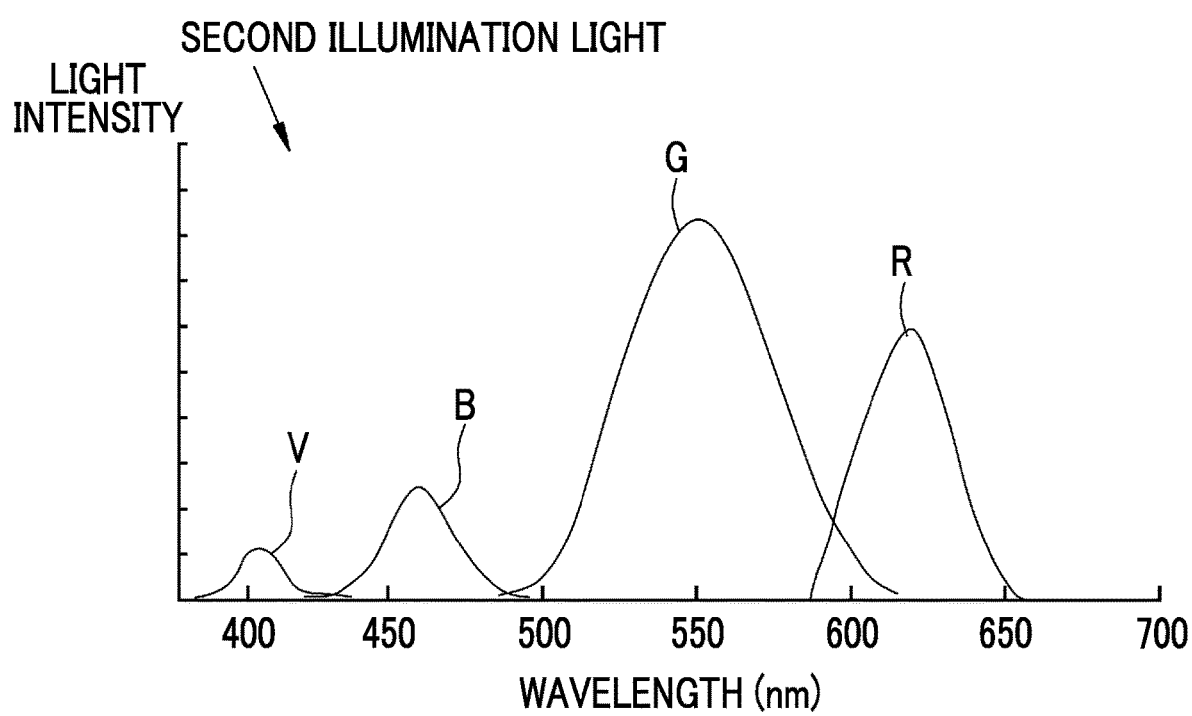
FIG. 6 is a graph showing the spectrum of second illumination light.

Further, in a case where the endoscope system 10 is set to the first b-observation mode, the light source controller 22 controls the respective LEDs 20a to 20d so that second illumination light of which a light intensity ratio between violet light V, blue light B, green light G, and red light R is Vs2:Bs2:Gs2:Rs2 is emitted. The light intensity ratio Vs2:Bs2:Gs2:Rs2 corresponds to the light amount condition of the second illumination light. It is preferable that the second illumination light enhances deep blood vessels. For this purpose, it is preferable that the light intensity of blue light B of the second illumination light is set to be higher than the light intensity of violet light V thereof. For example, as shown in FIG. 6, a ratio of the light intensity Vs2 of violet light V to the light intensity Bs2 of blue light B is set to "1:3".

Furthermore, in a case where the endoscope system 10 is set to the first ab-observation mode, the light source controller 22 performs a control to emit the first illumination light and the second illumination light for light emission periods of a first period and a second period, respectively, and to automatically switch and emit the first illumination light and the second illumination light, on the basis of the setting of the light emission period-setting unit 26. Each of the first and second periods has a light emission period of at least one or more frames.

Figure 7:
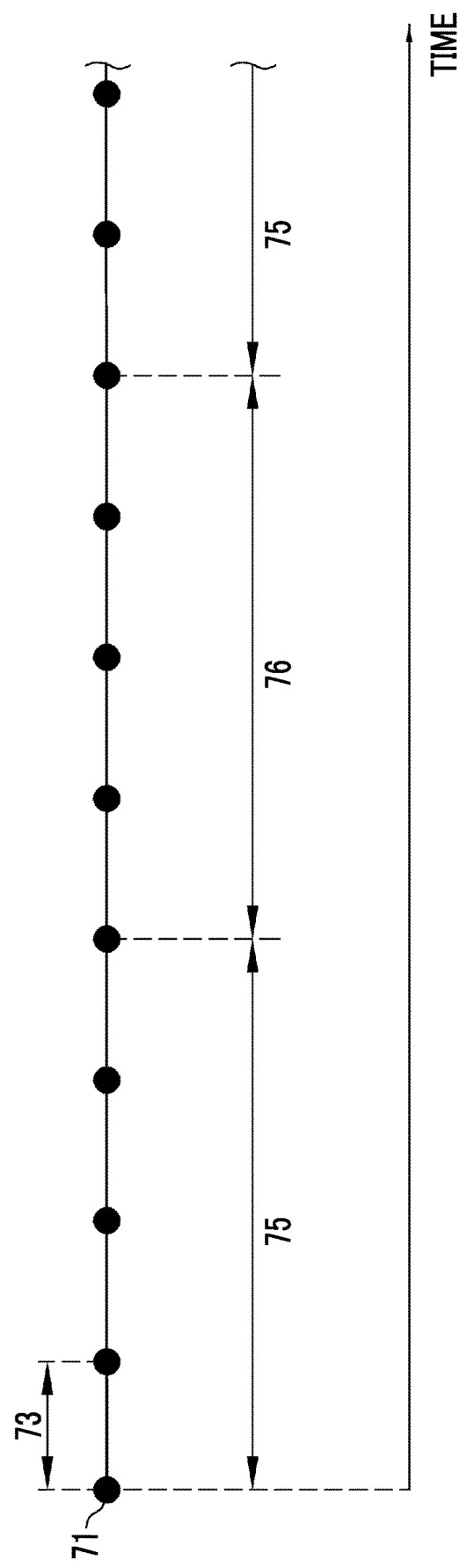
FIG. 7 is a diagram illustrating frames and light emission periods of first illumination light and second illumination light.

As shown in FIG. 7, in a case where, for example, the light source controller 22 sets the first period 75 to four frames and sets the second period 76 to four frames on the basis of the settings of the light emission period-setting unit 26 while using a frame 73, which is a unit of image pickup in which the emission 71 of illumination light starts, as a unit, the second illumination light continues to be emitted for four frames after the first illumination light continues to be emitted for four frames. Then, this light emission pattern is repeated. Reference numeral is given to only one of the emission 71 of illumination light in FIG. 7 in order to avoid complicating the drawing.

"Frame" means a unit used to control an image pickup sensor 48 (see FIG. 3) that picks up the image of an object to be observed. For example, "one frame" means a period including at least an exposure period in which the image pickup sensor 48 is exposed to light emitted from an object to be observed and a read-out period in which image signals are read out. The first period or the second period is determined so as to correspond to "frame" that is a unit of image pickup. The first period that is the light emission period of the first illumination light and the second period that is the light emission period of the second illumination light can be appropriately changed by the light emission period-setting unit 26, which is connected to the light source controller 22, on the basis of, for example, the operation of the console 19.

The base color tone of each of observation images to be displayed in observation modes included in the first observation mode group, which includes the first observation mode, the first a-observation mode, the first b-observation mode, and the first ab-observation mode, is the first base color tone, and the observation images have the same base color tone. Examples of a method of making the base color tones be the same in these observation modes include a method of adjusting illumination light in each observation mode, a method of performing image processing on images to be obtained, or the like.

For example, image processing is performed on an image to be obtained in an observation mode included in the first observation mode group, so that the base color tone of the image is set to the first base color tone. Examples of a method of performing image processing on images to be obtained include a method of performing white balance processing on a first a-image and a first b-image using specific gain coefficients in the respective observation modes, that is, the first a-observation mode, the first b-observation mode, and the first ab-observation mode to obtain observation images having the same natural color tone as in the first observation mode. In this case, it is assumed that the specific gain coefficients are corrected using observation images acquired in the past. For example, a gain coefficient for a subsequent first a-image is corrected in the first a-image using the first b-image. Further, a gain coefficient for a subsequent first b-image is corrected in the first b-image using the first a-image. An observation image to be obtained in an observation mode included in the first observation mode group can be changed to an observation image having the first base color tone, which is a natural color tone, by such a method.

Figure 8:
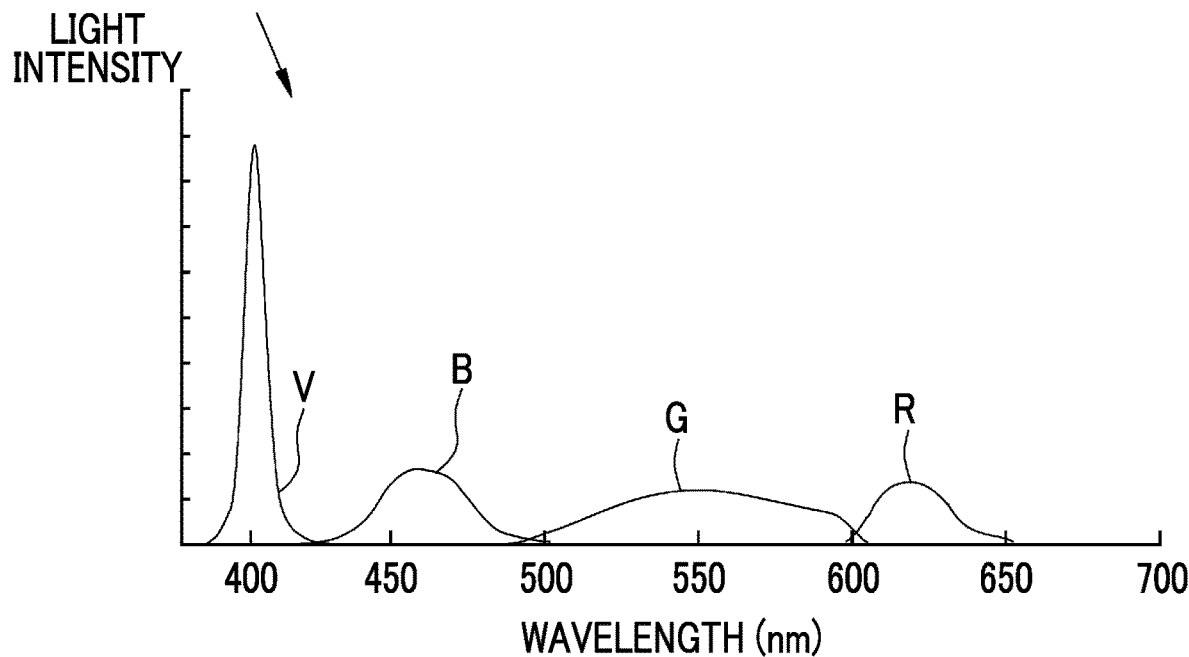
FIG. 8 is a graph showing the spectrum of third illumination light.

Furthermore, in a case where the endoscope system 10 is set to the second a-observation mode, the light source controller 22 controls the respective LEDs 20a to 20d so that third illumination light of which a light intensity ratio between violet light V, blue light B, green light G, and red light R is Vs3:Bs3:Gs3:Rs3 is emitted. The light intensity ratio Vs3:Bs3:Gs3:Rs3 corresponds to the light amount condition of the third illumination light. It is preferable that the third illumination light enhances superficial blood vessels. For this purpose, it is preferable that the light intensity of violet light V of the third illumination light is set to be higher than the light intensity of blue light B thereof. For example, as shown in FIG. 8, a ratio of the light intensity Vs3 of violet light V to the light intensity Bs3 of blue light B is set so that the light intensity Vs3 of violet light V is increased.

Figure 9:
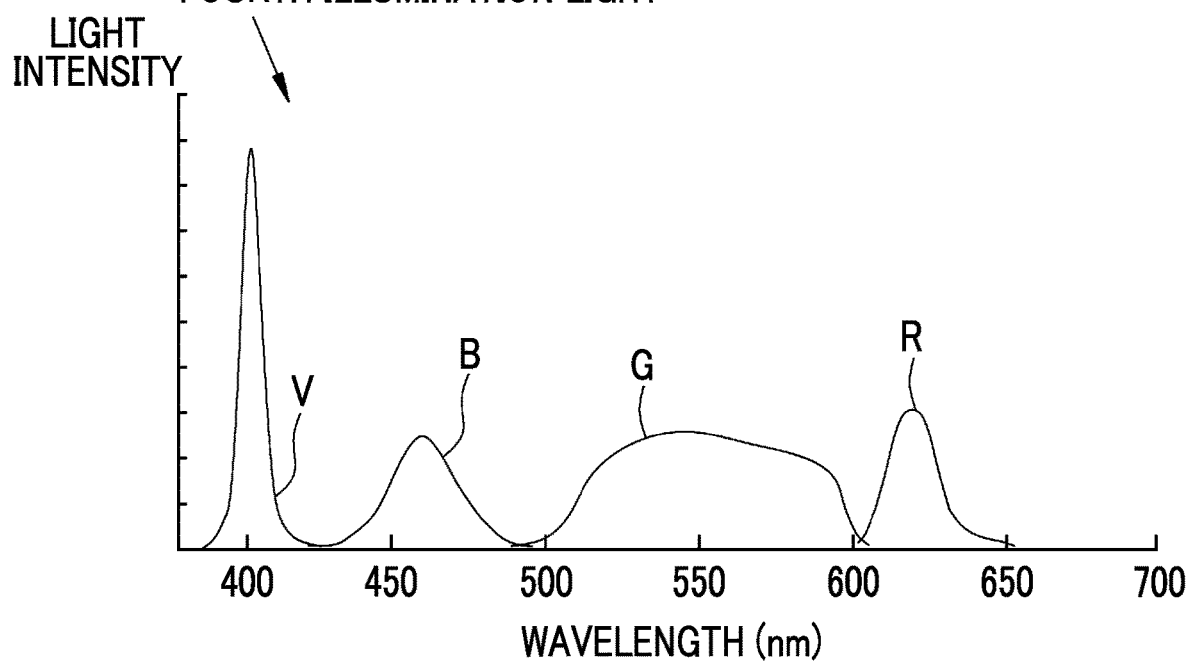
FIG. 9 is a graph showing the spectrum of fourth illumination light.

Further, in a case where the endoscope system 10 is set to the second b-observation mode, the light source controller 22 controls the respective LEDs 20a to 20d so that fourth illumination light of which a light intensity ratio between violet light V, blue light B, green light G, and red light R is Vs4:Bs4:Gs4:Rs4 is emitted. The light intensity ratio Vs4:Bs4:Gs4:Rs4 corresponds to the light amount condition of the fourth illumination light. It is preferable that the fourth illumination light enhances superficial blood vessels and makes an image bright even in a distant view. For this purpose, it is preferable that the light intensities of blue light B, green light G, and red light R of the fourth illumination light are set to be slightly higher than the light intensities of blue light B, green light G, and red light R of the third illumination light. For example, as shown in FIG. 9, the light intensity Bs4 of blue light B, the light intensity Gs4 of green light G, and the light intensity Rs4 of red light R are set to be slightly higher than the light intensity of blue light B, the light intensity of green light G, and the light intensity of red light R of the third illumination light.

Furthermore, in a case where the endoscope system 10 is set to the second ab-observation mode, the light source controller 22 performs a control to emit the third illumination light and the fourth illumination light for light emission periods of a third period and a fourth period, respectively, and to automatically switch and emit the third illumination light and the fourth illumination light, on the basis of the setting of the light emission period-setting unit 26. Each of the third and fourth periods has a light emission period of at least one or more frames.

Figure 10:
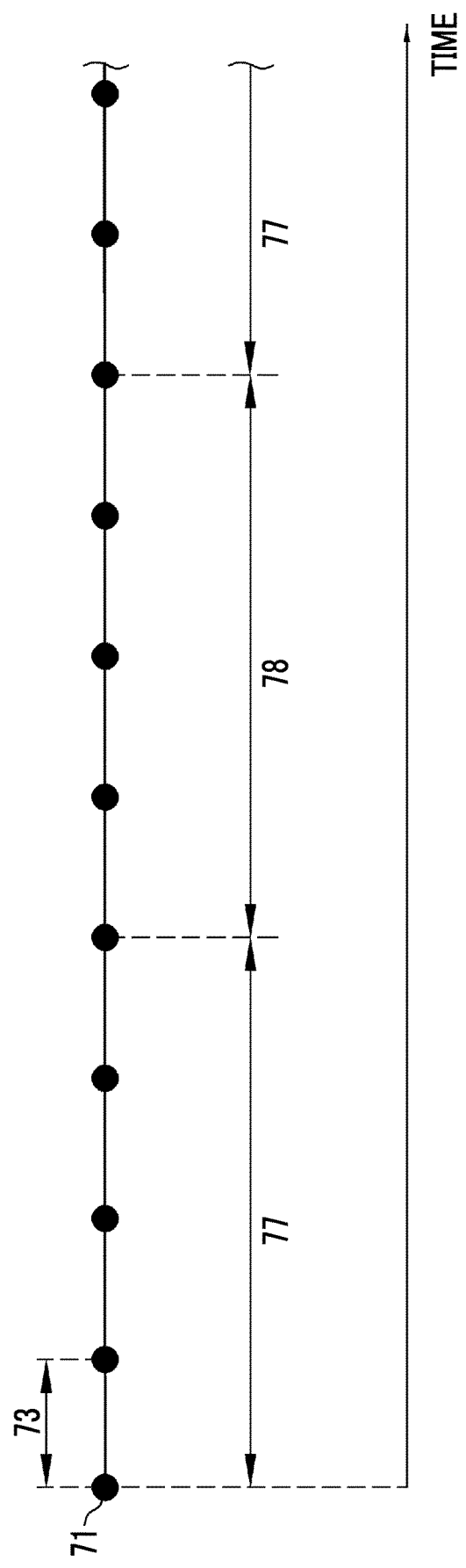
FIG. 10 is a diagram illustrating frames and light emission periods of third illumination light and fourth illumination light.

As shown in FIG. 10, in a case where, for example, the light source controller 22 sets a third period 77 to four frames and sets the fourth period 78 to four frames on the basis of the settings of the light emission period-setting unit 26 while using a frame 73, which is a unit of image pickup in which the emission 71 of illumination light starts, as a unit, the fourth illumination light continues to be emitted for four frames after the third illumination light continues to be emitted for four frames. Then, this light emission pattern is repeated. Reference numeral is given to only one of the emission 71 of illumination light in FIG. 10 in order to avoid complicating the drawing.

The third period or the fourth period is determined so as to correspond to "frame" that is a unit of image pickup. The third period that is the light emission period of the third illumination light and the fourth period that is the light emission period of the fourth illumination light can be appropriately changed by the light emission period-setting unit 26, which is connected to the light source controller 22, on the basis of, for example, the operation of the console 19.

The base color tone of each of observation images to be displayed in observation modes included in the second observation mode group, which includes the second a-observation mode, the second b-observation mode, and the second ab-observation mode, is the second base color tone, and the observation images have the same base color tone. For example, illumination light is adjusted in an observation mode included in the second observation mode group, so that a base color tone is set to the second base color tone.

For example, illumination light for making the base color tone of an observation image to be obtained in an observation mode included in the second observation mode group, which includes the second a-observation mode, the second b-observation mode, and the second ab-observation mode, be the second base color tone is used in a method of adjusting illumination light. Accordingly, an observation image to be obtained in an observation mode included in the second observation mode group is made to be an observation image having the second base color tone that is a color tone in which, for example, the structures of a mucosal surface layer, such as microscopic blood vessels, are enhanced and red components are few.

As shown in FIG. 3, the light guide 41 is built in the endoscope 12 and a universal cord (a cord connecting the endoscope 12 to the light source device 14 and the processor device 16), and transmits the pieces of light, which are combined by the optical path-combination unit 24, to the distal end part 12d of the endoscope 12.

The distal end part 12d of the endoscope 12 is provided with an illumination optical system 30a and an image pickup optical system 30b. The illumination optical system 30a includes an illumination lens 45, and an object to be observed is irradiated with light transmitted from the light guide 41 through the illumination lens 45. The image pickup optical system 30b includes an objective lens 46 and the image pickup sensor 48. Light reflected from the object to be observed is incident on the image pickup sensor 48 through the objective lens 46. Accordingly, the reflected image of the object to be observed is formed on the image pickup sensor 48.

The image pickup sensor 48 is a color image pickup sensor, and picks up the reflected image of an object to be examined and outputs image signals. It is preferable that the image pickup sensor 48 is a charge coupled device (CCD) image pickup sensor, a complementary metal-oxide semiconductor (CMOS) image pickup sensor, or the like. The image pickup sensor 48 used in the embodiment of the present invention is a color image pickup sensor used to obtain RGB image signals corresponding to three colors of R (red), G (green), and B (blue), that is, a so-called RGB image pickup sensor that comprises R pixels provided with R filters, G pixels provided with G filters, and B pixels provided with B filters.

Figure 11:
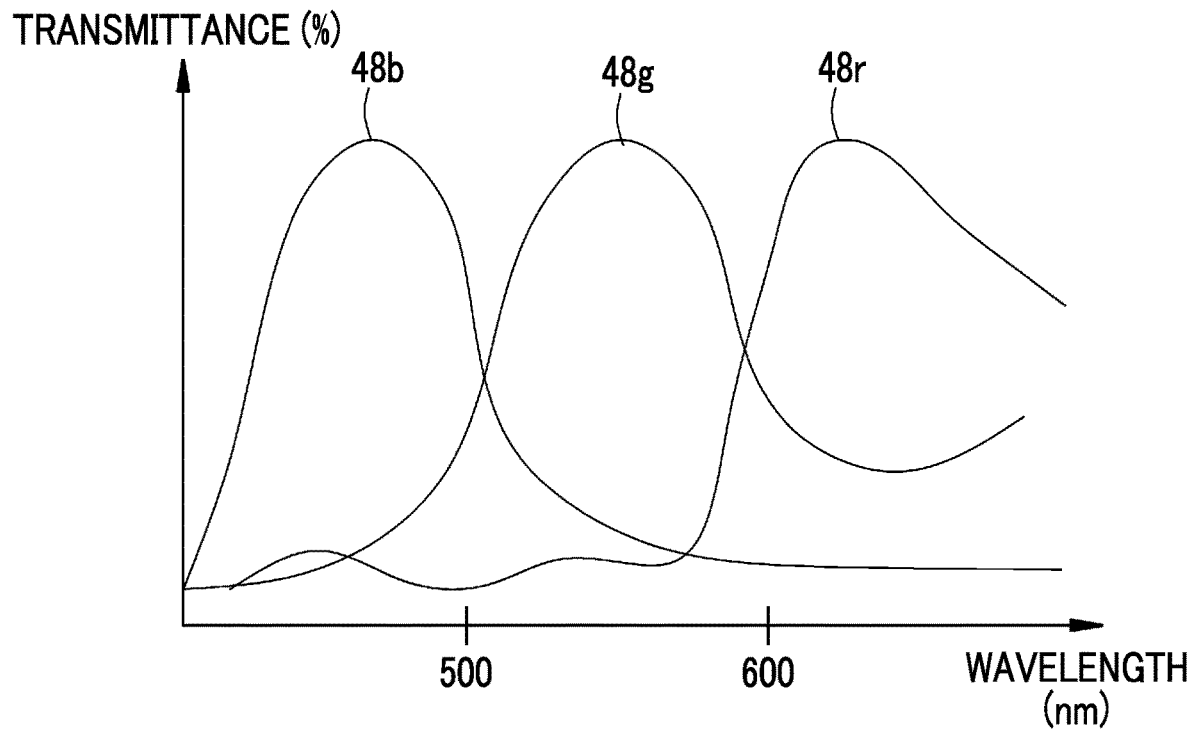
FIG. 11 is a diagram illustrating color filters included in an image pickup sensor.

As shown in FIG. 11, the B filter 48b transmits light of a violet-light wavelength range, light of a blue-light wavelength range, and short-wavelength light of light of a green-light wavelength range. The G filter 48g transmits light of a green-light wavelength range, long-wavelength light of light of a blue-light wavelength range, and short-wavelength light of light of a red-light wavelength range. The R filter 48r transmits light of a red-light wavelength range and long-wavelength light of a green-light wavelength range. Accordingly, in the image pickup sensor 48, the B pixel has sensitivity to violet light V and blue light B, the G pixel has sensitivity to blue light B, green light G, and red light R, and the R pixel has sensitivity to green light G and red light R.

The image pickup sensor 48 may be a so-called complementary color image pickup sensor, which comprises complementary color filters corresponding to C (cyan), M (magenta), Y (yellow), and G (green), instead of an RGB color image pickup sensor. In a case where a complementary color image pickup sensor is used, image signals corresponding to four colors of C, M, Y, and G are output. Accordingly, the image signals corresponding to four colors of C, M, Y, and G need to be converted into image signals corresponding to three colors of R, G, and B by complementary color-primary color conversion. Further, the image pickup sensor 48 may be a monochrome image pickup sensor that includes no color filter. In this case, since the light source controller 22 causes blue light B, green light G, and red light R to be emitted in a time-sharing manner, demosaicing needs to be added to processing for image pickup signals.

As shown in FIG. 3, the image signals output from the image pickup sensor 48 are transmitted to a CDS/AGC circuit 50. The CDS/AGC circuit 50 performs correlated double sampling (CDS) or auto gain control (AGC) on the image signals that are analog signals. The image signals, which have been transmitted through the CDS/AGC circuit 50, are converted into digital image signals by an analog/digital converter (A/D converter) 51. The digital image signals, which have been subjected to A/D conversion, are input to the processor device 16.

The processor device 16 comprises an image acquisition unit 52, a digital signal processor (DSP) 54, a noise removing unit 57, a central controller 58, an image processing unit 61, and a display controller 65. The image acquisition unit 52 acquires an observation image that is obtained in a case where the image of the object to be observed is picked up in the endoscope 12. Specifically, digital color image signals obtained from the endoscope 12 are input to the image acquisition unit 52 as an observation image. The color image signals are formed of red color signals output from the R pixels of the image pickup sensor 48, green color signals output from the G pixels of the image pickup sensor 48, and blue color signals output from the B pixels of the image pickup sensor 48.

The DSP 54 performs various kinds of signal processing, such as defect correction processing, offset processing, white balance processing, linear matrix processing, gamma conversion processing, and demosaicing processing, on the received image signals.

Signals of defective pixels of the image pickup sensor 48 are corrected in the defect correction processing. Dark current components are removed from the image signals having been subjected to the defect correction processing in the offset processing, so that an accurate zero level is set.

Linear matrix processing for improving color reproducibility is performed on the image signals having been subjected to the white balance processing. After that, brightness or a chroma saturation is adjusted by the gamma conversion processing. The demosaicing processing (also referred to as equalization processing or demosaicing) is performed on the image signals having been subjected to the linear matrix processing, so that signals of colors deficient in each pixel are generated by interpolation. All the pixels are made to have the signals of the respective colors by this demosaicing processing.

The noise removing unit 57 performs noise removal processing (for example, a moving-average method, a median filtering method, or the like) on the image signals, which have been subjected to gamma correction and the like by the DSP 54, to remove noise from the image signals. After noise is removed, the image signals are transmitted to the image processing unit 61.

Figure 12:
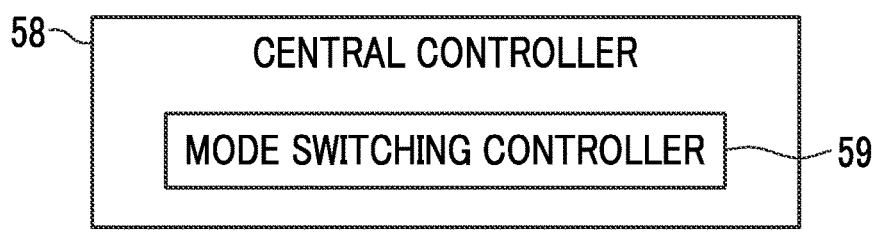
FIG. 12 is a block diagram showing the functions of a central controller.

The central controller 58 receives information from the endoscope 12 or the console 19, and controls the respective units of the processor device 16 and the light source device 14 on the basis of the received information. As shown in FIG. 12, the central controller 58 comprises a mode switching controller 59. The mode switching controller 59 performs a control to switch an observation mode according to the first operation or the second operation that is performed by the mode changeover switch 12g, the auxiliary mode changeover switch 12f, or the like.

Figure 13:
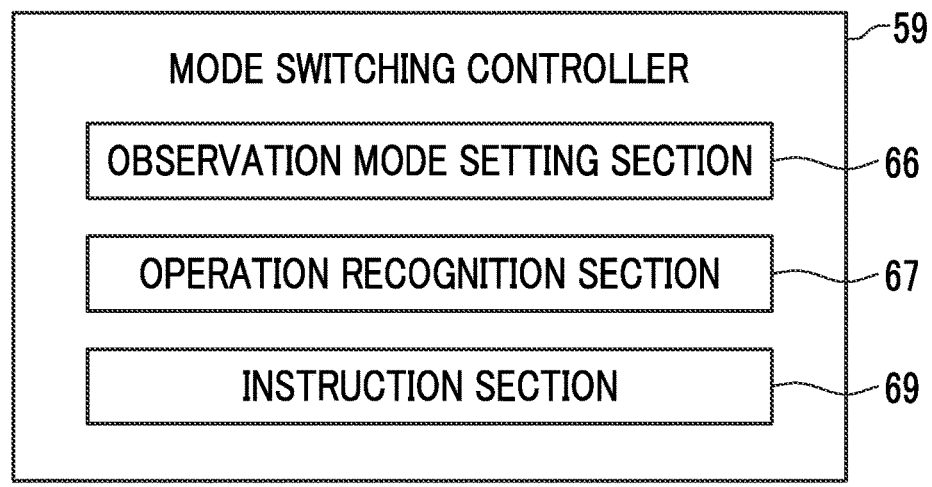
FIG. 13 is a block diagram showing the functions of a mode switching controller.

As shown in FIG. 13, the mode switching controller 59 comprises observation mode setting section 66, an operation recognition section 67, and an instruction section 69. In a case where an observation is made, the observation mode setting section 66 sets observation modes to be selected among the plurality of observation modes, an order in which the selected observation modes are to be switched, and the aspect of a display on the display 18 in each selected observation mode or switching processing or the like to be set for the first operation or the second operation. The respective sections, such as the operation recognition section 67 and the instruction section 69, share the setting items of the observation mode setting section 66 by the mode switching controller 59. The operation recognition section 67 recognizes an operation that is performed by the mode changeover switch 12g, the auxiliary mode changeover switch 12f, or the like to be used for the switching of a mode. The instruction section 69 instructs the respective units of the endoscope system 10 through the central controller 58 so that an observation mode is appropriately switched.

In a case where an observation is made in the endoscope system 10, the observation mode setting section 66 sets the respective observation modes, which are included in the plurality of observation modes, as a main observation mode and/or a sub-observation mode at the time of switching of the plurality of observation modes. Accordingly, the plurality of observation modes to be used for observation include a plurality of main observation modes and at least one sub-observation mode.

The plurality of main observation modes are switched in a predetermined order. The plurality of main observation modes are switched by main switching processing. Switching between at least one sub-observation mode and a specific main observation mode of the plurality of main observation modes is performed by sub-switching processing. The observation mode setting section 66 sets any one main observation mode, which is to be set as a specific main observation mode, among the plurality of main observation modes. Further, the observation mode setting section 66 presets a combination of a specific main observation mode and a sub-observation mode that are to be switched by sub-switching processing.

Figure 14:
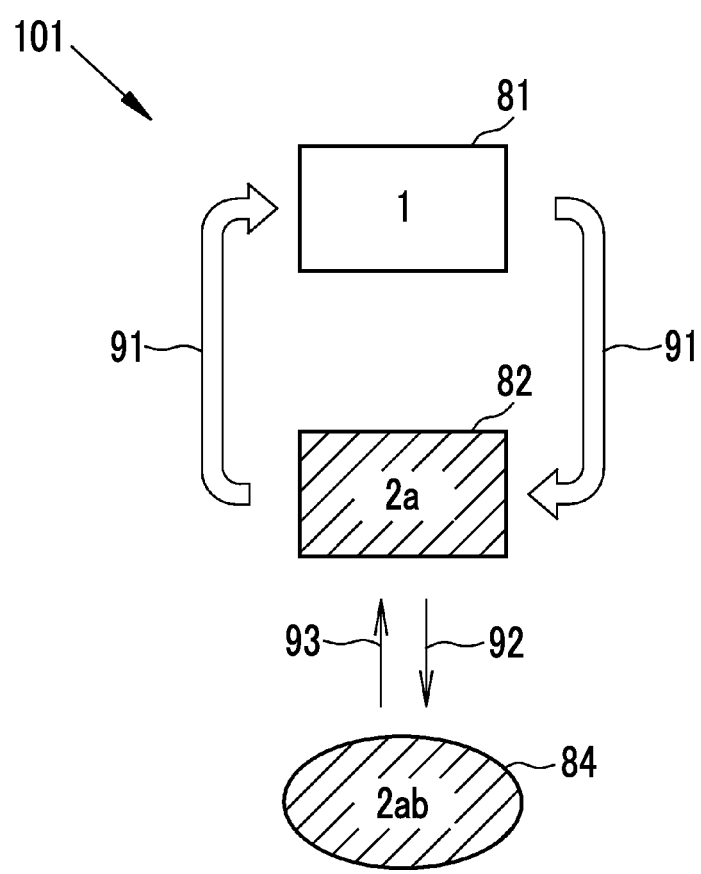
FIG. 14 is a diagram illustrating a first pattern of the flow of an observation mode.

As shown in FIG. 14, for example, a first observation mode 81 and the second a-observation mode 82 are set as the main observation modes in a first pattern 101 in which the first observation mode 81 and the second a-observation mode are alternately switched as the main observation modes. The first pattern 101 is an example of a type of flow of the switching of the observation modes. Among the observation modes, the second a-observation mode 82 is set as a specific main observation mode and a second ab-observation mode 84 is set as a sub-observation mode. In FIG. 14, thick arrows indicate main switching processing for switching the main observation modes, and thin arrows indicate sub-switching processing for performing switching between a specific main observation mode and a sub-observation mode. Further, in order to avoid complicating drawings, hereinafter, in the drawings, the first observation mode 81 will be shown as 1, a first ab-observation mode 85 will be shown as 1*ab*, a first a-observation mode 86 will be shown as 1*a*, a first b-observation mode 87 will be shown as 1*b*, the second a-observation mode 82 will be shown as 2*a*, and the second ab-observation mode 84 will be shown as 2*ab*. Further, likewise, as for even the observation images obtained in the respective observation modes, in the columns of the observation images in the drawings, a first image will be shown as 1, the first a-image will be shown as 1*a*, the first b-image will be shown as 1*b*, a second a-image will be shown as 2*a*, and a second b-image will be shown as 2*b*.

In FIG. 14, an order is preset as the first pattern 101 so that the first observation mode 81 and the second a-observation mode 82 are alternately switched as the main observation modes. Since the main switching processing is performed according to the first operation, the first observation mode 81 and the second a-observation mode 82 are alternately switched by the first operation. Since the second a-observation mode 82 is set as a specific main observation mode, the second a-observation mode 82 and the second ab-observation mode 84 are switched in a case where the second operation is performed during an observation that is made in the second a-observation mode 82.

In the combination of a specific main observation mode and a sub-observation mode, an observation image displayed in a specific main observation mode and an observation image displayed in a sub-observation mode combined with this specific main observation mode have the same base color tone. The base color tone includes the first base color tone and the second base color tone. Accordingly, in a case where the observation image to be displayed in a specific main observation mode has the first base color tone, a sub-observation mode in which an observation image to be displayed has the first base color tone is combined. Further, in a case where the observation image to be displayed in a specific main observation mode has the second base color tone, a sub-observation mode in which an observation image to be displayed has the second base color tone is combined. That is, a specific main observation mode and a sub-observation mode are selected from the respective observation modes included in the first observation mode group and are combined with each other, and a specific main observation mode and a sub-observation mode are selected from the respective observation modes included in the second observation mode group and are combined with each other.

In FIG. 14, the second a-observation mode 82 and the second ab-observation mode 84 are observation modes in which observation images to be displayed have the same second base color tone. Hereinafter, an observation mode in which an observation image to be displayed has the second base color tone will be shown with diagonal lines in the drawings.

The operation recognition section 67 recognizes the first operation or the second operation that is performed by the mode changeover switch 12*g*, the auxiliary mode changeover switch 12*f*, or the like. In a case where there are a plurality of types of operations as each of the first operation and the second operation, at least one type of operation among the operations is preset as the specific operation of the first operation or the second operation. The operation recognition section 67 recognizes the set operation and transmits the execution of the first operation or the second operation to the instruction section 69. Examples of the first operation or the second operation using a scope switch, such as the mode changeover switch 12*g*, include a single press operation for pressing the mode changeover switch 12*g* for a time less than a certain time, a long press operation for pressing the mode changeover switch 12*g* for a time equal to or longer than the certain time, or a long press release operation for releasing the mode changeover switch 12*g*, which is being subjected to the long press operation, during the long press operation. In addition, examples of the first operation or the second operation include a double click operation in which a series of operations for pressing and releasing the mode changeover switch 12*g* is detected at least twice and this plurality of the series of operations are performed in a preset specific click determination time, a half-press operation in a case where the mode changeover switch 12*g* is a switch that can be pressed in stages, or the like.

It is preferable that both the first operation and the second operation are performed by a specific operation part. For example, in a case where the specific operation part is the mode changeover switch 12*g*, the first operation is set to a single press operation for pressing the mode changeover switch 12*g* for a time less than a certain time and the second operation is set to a long press operation for pressing the mode changeover switch 12*g* for a time equal to or longer than the certain time or a long press release operation for releasing the mode changeover switch 12*g*, which is being subjected to the long press operation, during the long press operation. This certain time is a long press determination time, and is preset. Accordingly, it is possible to conveniently perform the first operation for switching the displays of observation images having different base color tones and the second operation for switching the displays of related observation images having the same base color tone by one operation part.

In FIG. 14, in a case where a single press operation 91 for pressing the mode changeover switch 12*g* for a time less than a certain time is set as the first operation and a long press operation 92 for pressing the mode changeover switch 12*g* for a time equal to or longer than the certain time or a long press release operation 93 for releasing the mode changeover switch 12*g*, which is being subjected to the long press operation, is set as the second operation, the main switching processing is performed by the single press operation of the mode changeover switch 12*g*. Accordingly, the first observation mode 81 and the second a-observation mode 82 are switched. Then, while the mode changeover switch 12*g* continues to be pressed for a time equal to or longer than the certain time during an observation made in the second a-observation mode 82, observation images are displayed in the second ab-observation mode 84. After that, the second ab-observation mode 84 is switched to the second a-observation mode 82 by the sub-switching processing performed by the long press release operation 93 for releasing the mode changeover switch 12*g*, which continues to be pressed.

Figure 15:
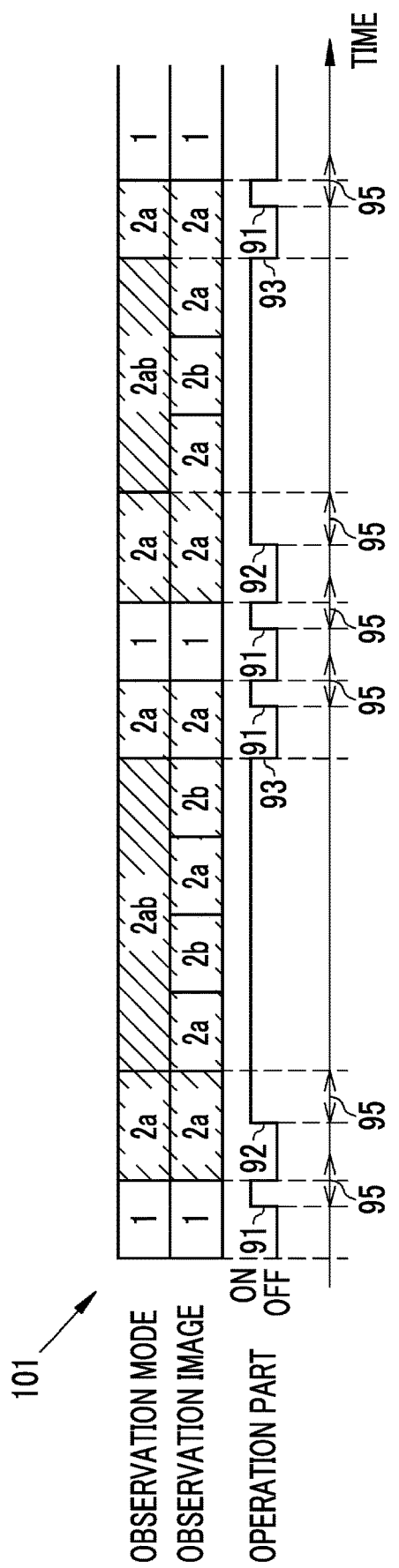
FIG. 15 is a diagram illustrating a relationship between an operation in the first pattern and the observation mode.

As shown in FIG. 15, in the first pattern 101, main switching processing is performed in the first observation mode 81 by the single press operation 91 for pressing the mode changeover switch 12*g* for a time less than the long press determination time 95. Accordingly, the first observation mode 81 is switched to the second a-observation mode 82. Since the second a-observation mode 82 is set to a specific main observation mode, the sub-switching processing is performed in the second a-observation mode 82 by the long press operation 92 for pressing the mode changeover switch 12g for a time equal to or longer than the long press determination time 95. Accordingly, the second a-observation mode 82 is switched to the second ab-observation mode 84. The second ab-observation mode 84 continues during the pressing of the mode changeover switch 12g, but is switched to the second a-observation mode 82, which is a specific main observation mode, by the long press release operation 93 for releasing the pressing of the mode changeover switch 12g. The main switching processing is performed in the second a-observation mode 82 by the single press operation 91, so that the second a-observation mode 82 is switched to the first observation mode 81. As described above, it is possible to perform the first operation and the second operation in a specific main observation mode by only one operation part, such as the mode changeover switch 12g. Accordingly, it is possible to conveniently shift an observation mode to an observation mode corresponding to the observer's desire.

The instruction section 69 instructs the respective units of the endoscope system 10 through the central controller 58 so that switching processing preset for the first operation or the second operation is performed. For example, in a case where the main switching processing is set for the first operation and the sub-switching processing is set for the second operation, the instruction section 69 instructs each unit to perform the main switching processing on the basis of the first operation recognized by the operation recognition section 67 and instructs each unit to perform the sub-switching processing on the basis of the second operation recognized by the operation recognition section 67. As described above, the mode switching controller 59 performs the main switching processing according to the first operation and performs the sub-switching processing according to the second operation.

As shown in FIG. 3, the image processing unit 61 performs color conversion processing, color enhancement processing, structure enhancement processing, and/or the like depending on each observation mode according to the instruction of the central controller 58 to generate an observation image. The central controller 58 gives an instruction on whether or not image processing is required, or the like to the image processing unit 61 by a control related to an observation mode that is performed by the mode switching controller 59.

The display controller 65 displays a specific observation image on the display 18 in a specific display aspect. The display controller 65 converts the observation image, which is generated by the image processing unit 61, into display format signals depending on each observation mode according to the instruction of the central controller 58, and displays the display format signals on the display 18. The central controller 58 gives various instructions to the display controller 65 by a control related to an observation mode that is performed by the mode switching controller 59 so that a specific observation image corresponding to each observation mode is displayed on the display 18 in a specific display aspect and the like.

The display aspect includes the automatic switching display aspect and the continuous display aspect. In the automatic switching display aspect, a plurality of observation images are automatically switched and displayed on the display 18. The order of switching, the speed of switching, or the like is preset. For example, as shown in FIG. 7 or 10, the observation mode is switched from the first a-observation mode or the second a-observation mode by four frames at a time. The order of switching may be started from, for example, the first b-observation mode or the second b-observation mode or may be started from a point of time when the previous observation mode ends. That is, in a case where an observation mode ends at the first a-observation mode in the previous first ab-observation mode, an observation mode may be started from the first b-observation mode in the next first ab-observation mode. Further, the number of frames to be displayed in one observation mode may also be changed by setting. For example, the first a-observation mode and the first b-observation mode may be set to be switched by the numbers of frames different from each other. In the continuous display aspect, an observation image is continuously displayed on the display 18.

In FIG. 14, observation images are displayed in the continuous display aspect in each of the first observation mode 81 and the second a-observation mode 82 and observation images are displayed in the automatic switching display aspect in the second ab-observation mode 84. In FIG. 14, the first observation mode 81 and the second a-observation mode 82, which are in the continuous display aspect, are shown by rectangular shapes and the second ab-observation mode 84, which is in the automatic switching display aspect, is shown by an elliptical shape. Even in the subsequent drawings, an observation mode, which is in the continuous display aspect, is shown by a rectangular shape and an observation mode, which is in the automatic switching display aspect, is shown by an elliptical shape.

In a case where the endoscope system 10 has a plurality of observation modes including a plurality of main observation modes and a sub-observation mode as described above, main switching processing for switching the plurality of main observation modes in a predetermined order is performed according to the first operation by the mode switching controller 59 and sub-switching processing for performing switching between a specific main observation mode of the plurality of main observation modes and a sub-observation mode is performed according to the second operation different from the first operation by the mode switching controller 59, a specific display aspect includes an automatic switching display aspect in which a plurality of observation images are automatically switched and displayed on the display 18 and a continuous display aspect in which an observation image is continuously displayed on the display 18, and the observation image displayed in the specific main observation mode and the observation image displayed in the sub-observation mode have the same base color tone.

Accordingly, the endoscope system 10 can flexibly perform complicated switching of a plurality of observation modes including related observation modes by performing the main switching processing and the sub-switching processing according to the first operation and the second operation. Further, since a display aspect includes the automatic switching display aspect and the continuous display aspect in addition to the main switching processing and the sub-switching processing, it is possible to make an observation according to a purpose, such as screening or detailed observation. Furthermore, since an observation image to be displayed in a specific main observation mode and an observation image to be displayed in a sub-observation mode are observation images having the same base color tone, for example, an observation image in which the structure of a superficial portion of a mucous membrane of an object to be observed is enhanced and an observation image in which the structure of a medium-deep portion is enhanced are displayed even in the automatic switching display aspect. Accordingly, it is easy to recognize different portions of both the observation images. Further, in a case where observation images are switched and displayed at a relatively high speed in the automatic switching display aspect, different portions of both the observation images are displayed three-dimensionally like an animation. Accordingly, the structures of the superficial portion and the medium-deep portion of the object to be observed can be recognized three-dimensionally. An object to be observed can be identified in the endoscope system 10 at a higher degree as described above, which contributes to a detailed and accurate diagnosis.

Next, the pattern of an observation mode of the endoscope system 10 will be exemplarily described. In the pattern of an observation mode, it is preferable that observation images are displayed on the display unit in the automatic switching display aspect in a specific main observation mode and an observation image is displayed on the display unit in the continuous display aspect in a sub-observation mode.

For example, a specific main observation mode is the first ab-observation mode in which two images, that is, the first a-image and the first b-image having the first base color tone are displayed on the display 18 in the automatic switching display aspect, and a sub-observation mode is any one of the first a-observation mode in which the first a-image having the first base color tone is displayed on the display 18 in the continuous display aspect or the first b-observation mode in which the first b-image having the first base color tone is displayed on the display 18 in the continuous display aspect.

In a second pattern 102 shown in FIGS. 16A and 16B, an observation image of the first a-observation mode 86 and an observation image of the first b-observation mode 87 are displayed on the display 18 in the automatic switching display aspect in the first ab-observation mode 85 in a specific main observation mode and, an observation image is displayed on the display 18 in the continuous display aspect in the first a-observation mode 86 in a sub-observation mode. As shown in FIGS. 16A and 16B, the switching of the main observation mode is performed by the single press operations 91 of the mode changeover switch 12g and the switching of a sub-observation mode is performed by the long press operation 92 and the long press release operation 93 of the mode changeover switch 12g. The first a-observation mode 86, which is a sub-observation mode shown in FIGS. 16A and 16B, may be the first b-observation mode 87.

Further, for example, a specific main observation mode is the second ab-observation mode in which two images, that is, the second a-image and the second b-image having the second base color tone are displayed on the display 18 in the automatic switching display aspect, and a sub-observation mode is any one of the second a-observation mode in which the second a-image having the second base color tone is displayed on the display 18 in the continuous display aspect or the second b-observation mode in which the second b-image having the second base color tone is displayed on the display 18 in the continuous display aspect. Furthermore, it is preferable that there are a plurality of specific main observation modes.

Figure 17:
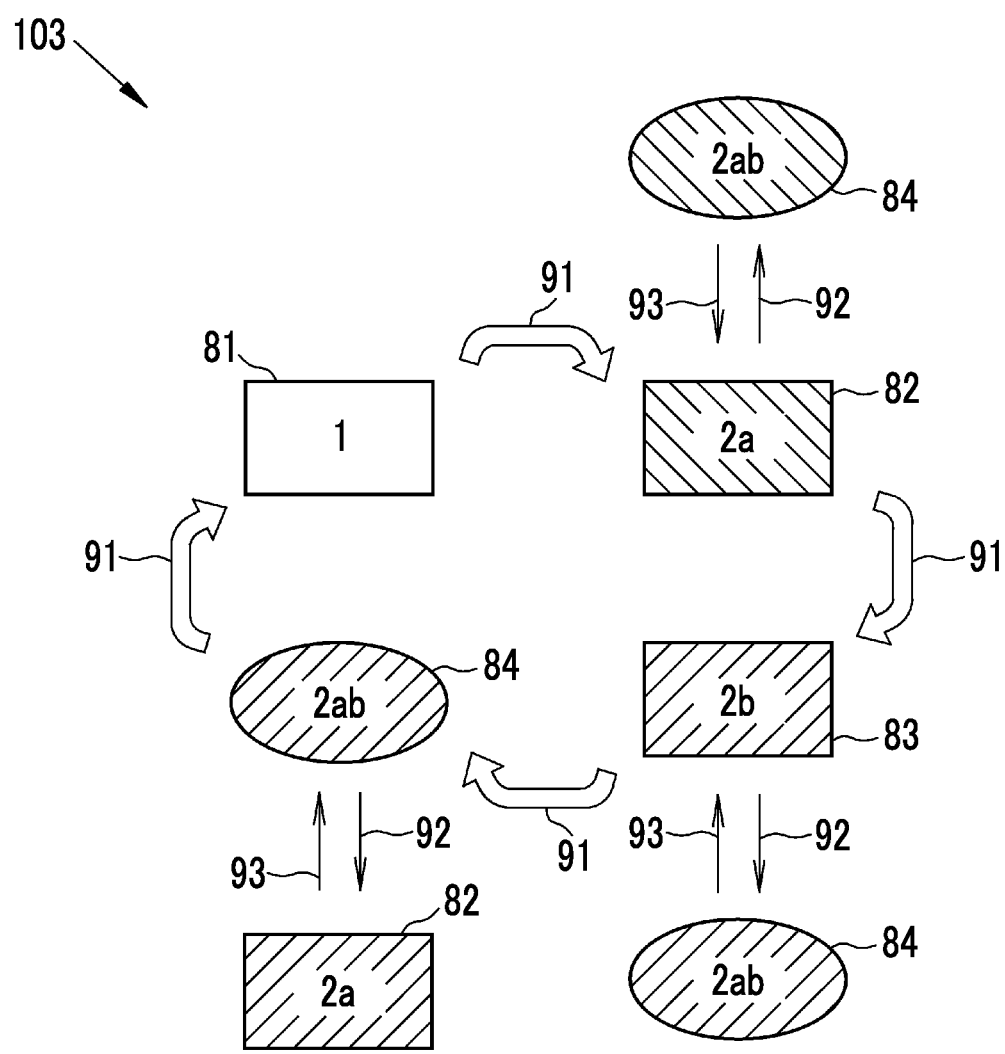
FIG. 17 is a diagram illustrating a third pattern of the flow of an observation mode.
Figure 18:
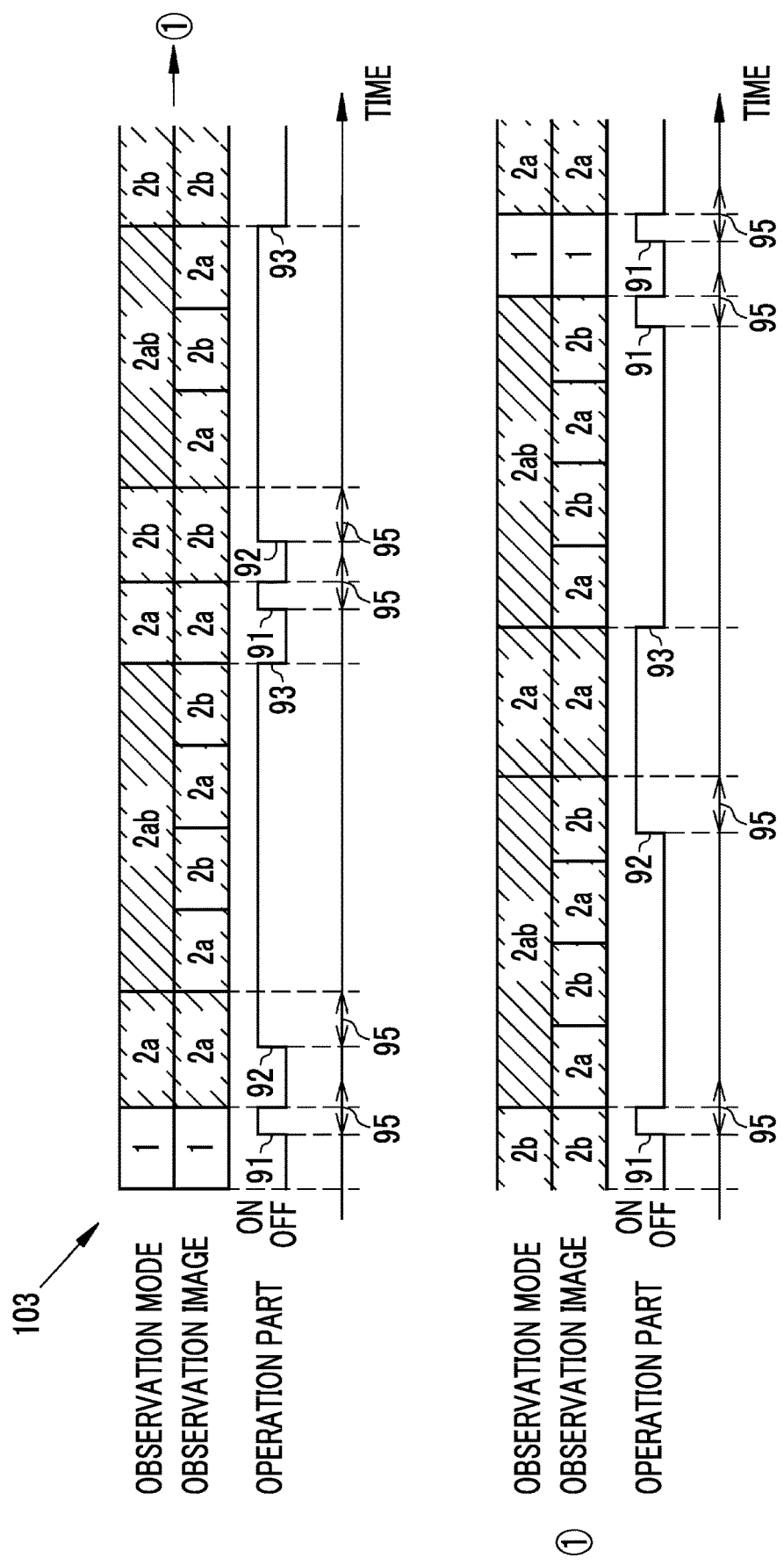
FIG. 18 is a diagram illustrating a relationship between an operation in the third pattern and the observation mode.

In a third pattern 103 shown in FIGS. 17 and 18, three specific main observation modes are provided. The three specific main observation modes are the second a-observation mode 82, the second b-observation mode 83, and the second ab-observation mode 84. In each of the second a-observation mode 82 and the second b-observation mode 83, an observation image is displayed on the display 18 in the continuous display aspect. Further, in the second ab-observation mode 84, the second a-image and the second b-image are displayed on the display 18 in the automatic switching display aspect. As shown on the upper row in FIG. 18, the first observation mode 81 is switched to the second a-observation mode 82 by the main switching processing that is performed by the single press operation 91 and the second a-observation mode 82 is switched to the second b-observation mode 83 by the main switching processing that is performed by the single press operation 91. The second b-observation mode 83 is switched to the second ab-observation mode 84 by the main switching processing that is performed by the single press operation 91. The second ab-observation mode 84 is returned to the first observation mode 81 by the main switching processing that is performed by the single press operation. Further, each of two specific main observation modes, that is, the second a-observation mode 82 and the second b-observation mode 83 comprises the second ab-observation mode 84 as a sub-observation mode. Furthermore, a specific main observation mode of the second ab-observation mode 84 comprises the second a-observation mode 82 as a sub-observation mode. The second b-observation mode 83 may be a sub-observation mode, which is to be combined with the second ab-observation mode 84, in addition to the second a-observation mode 82.

Further, in the pattern of an observation mode, it is preferable that an observation image is displayed on the display 18 in the continuous display aspect in a specific main observation mode and observation images are displayed on the display 18 in the automatic switching display aspect in a sub-observation mode.

For example, a specific main observation mode is any one of the first a-observation mode in which the first a-image having the first base color tone is displayed on the display 18 in the continuous display aspect or the first b-observation mode in which the first b-image is displayed on the display 18 in the continuous display aspect, and a sub-observation mode is the first ab-observation mode in which two images, that is, the first a-image and the first b-image having the first base color tone are displayed on the display 18 in the automatic switching display aspect.

In a fourth pattern 104 shown in FIGS. 19A and 19B, the first a-image is displayed on the display 18 in the continuous display aspect in the first a-observation mode 86 in a specific main observation mode and the first a-image and the first b-image are automatically switched and displayed on the display 18 in the automatic switching display aspect in the first ab-observation mode 85 in a sub-observation mode. As shown in FIGS. 19A and 19B, the switching of the main observation mode is performed by the single press operation 91 of the mode changeover switch 12g and the switching of a sub-observation mode is performed by the long press operation 92 and the long press release operation 93 of the mode changeover switch 12g. The first a-observation mode 86, which is a specific main observation mode in FIGS. 19A and 19B, may be the first b-observation mode 87.

Further, for example, a specific main observation mode is the first observation mode in which the first image having the first base color tone is displayed on the display 18 in the continuous display aspect and a sub-observation mode is the first ab-observation mode in which two images, that is, the first a-image and the first b-image having the first base color tone are displayed on the display 18 in the automatic switching display aspect.

Figure 20A:
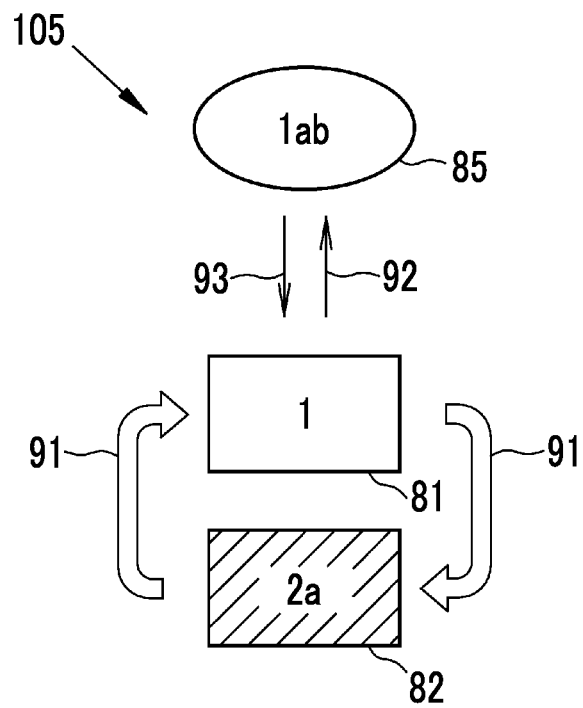
FIG. 20A is a diagram illustrating a fifth pattern of the flow of an observation mode and FIG. 20B is a diagram illustrating a relationship between an operation in the fifth pattern and the observation mode.
Figure 20B:
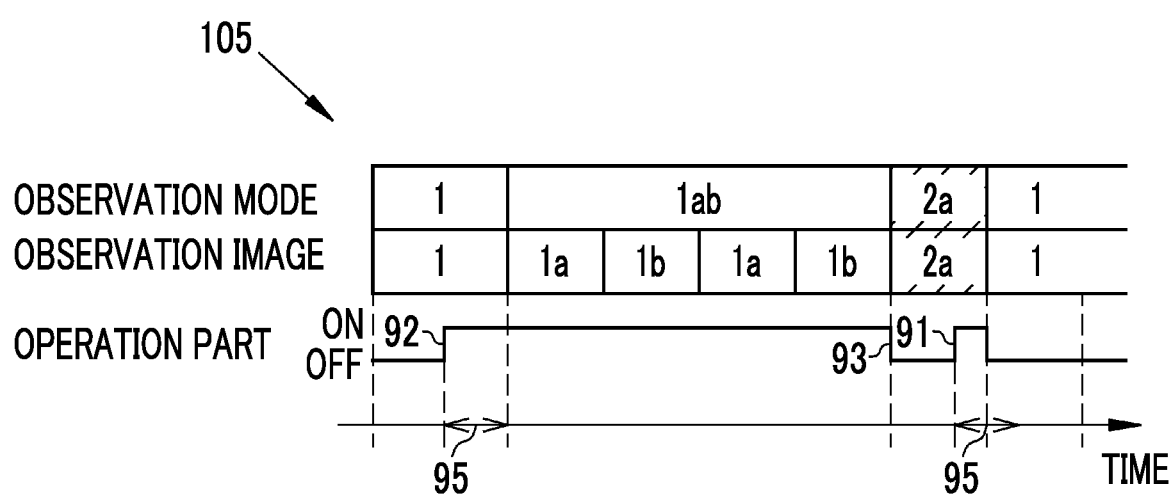

In a fifth pattern 105 shown in FIGS. 20A and 20B, the first image is displayed on the display 18 in the continuous display aspect in the first observation mode 81 in a specific main observation mode and the first a-image and the first b-image are automatically switched and displayed on the display 18 in the automatic switching display aspect in the first ab-observation mode 85 in a sub-observation mode. As shown in FIGS. 20A and 20B, the switching of the main observation mode is performed by the single press operation 91 of the mode changeover switch 12g and the switching of a sub-observation mode is performed by the long press operation 92 and the long press release operation 93 of the mode changeover switch 12g. The second a-observation mode 82, which is the main observation mode other than a specific main observation mode shown in FIGS. 20A and 20B, may be the second b-observation mode 83.

Figure 21:
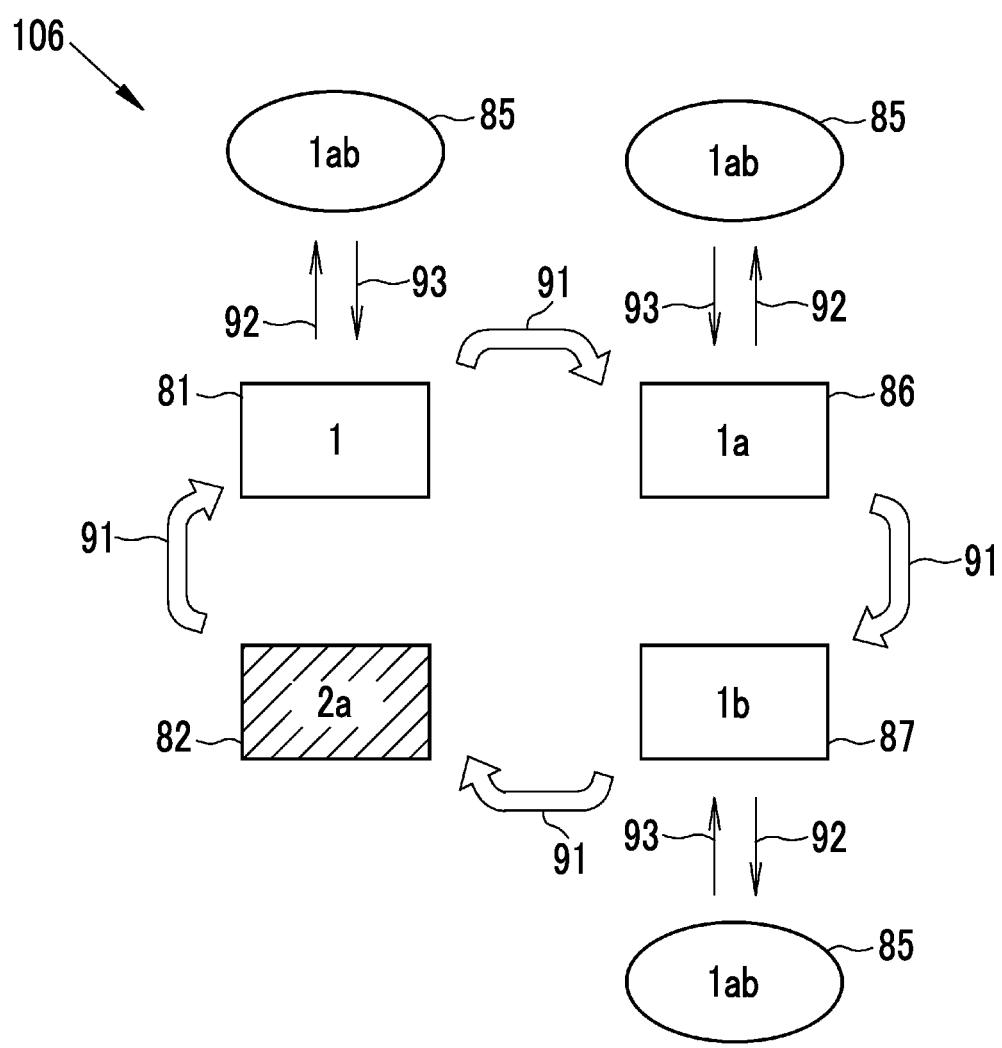
FIG. 21 is a diagram illustrating a sixth pattern of the flow of an observation mode.
Figure 22:
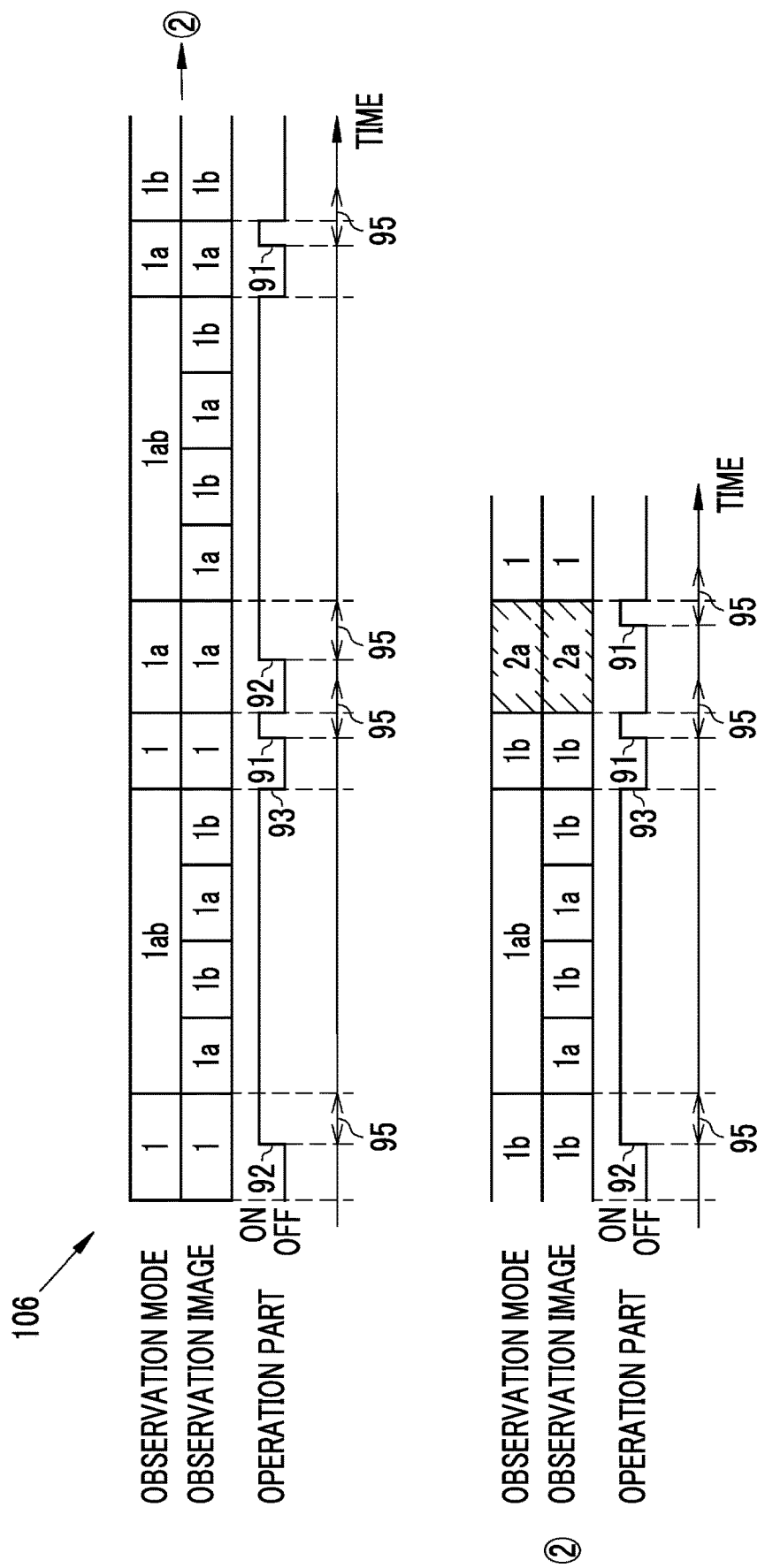
FIG. 22 is a diagram illustrating a relationship between an operation in the sixth pattern and the observation mode.

A sixth pattern 106 shown in FIGS. 21 and 22 is a pattern in which the fourth pattern including a combination where a specific main observation mode is the first a-observation mode 86 and a sub-observation mode is the first observation mode is added to the fifth pattern including a combination where a specific main observation mode is the first observation mode 81 and a sub-observation mode is the first ab-observation mode 85. Accordingly, the sixth pattern 106 comprises four main observation modes and three among them are specific main observation modes. The specific main observation modes are the first observation mode 81, the first a-observation mode 86, and the first b-observation mode 87, and each of the specific main observation modes comprises the first ab-observation mode 85 as a sub-observation mode. In FIGS. 21 and 22, the main observation modes are arranged in the order of the first observation mode 81, the first a-observation mode 86, the first b-observation mode 87, and the second a-observation mode 82. However, for example, the first b-observation mode 87 may follow after the first observation mode 81. Further, the second b-observation mode 83 may be provided instead of the second a-observation mode 82.

Further, for example, a specific main observation mode is any one of the second a-observation mode in which the second a-image having the second base color tone is displayed on the display 18 in the continuous display aspect or the second b-observation mode in which the second b-image having the second base color tone is displayed on the display 18 in the continuous display aspect, and a sub-observation mode is the second ab-observation mode in which two images, that is, the second a-image and the second b-image having the second base color tone are displayed on the display 18 in the automatic switching display aspect.

A seventh pattern 107 shown in FIGS. 23A and 23B comprises three main observation modes and two among them are specific main observation modes. The specific main observation modes are the second a-observation mode 82 and the second b-observation mode 83 and each of the specific main observation modes comprises the second ab-observation mode 84 as a sub-observation mode. In FIGS. 21 and 22, the main observation modes are arranged in the order of the first observation mode 81, the second a-observation mode 82, and the second b-observation mode 83. However, the main observation modes may be arranged in the order of, for example, the first observation mode 81, the second b-observation mode 83, and the second a-observation mode 82.

Further, for example, a specific main observation mode is any one of the first observation mode in which the first image having the first base color tone is displayed on the display 18 in the continuous display aspect or the second a-observation mode or the second b-observation mode in which the second a-image or the second b-image having the second base color tone is displayed on the display 18 in the continuous display aspect, and a sub-observation mode is the first ab-observation mode in which the first a-image and the first b-image are displayed on the display 18 in the automatic switching display aspect in the first observation mode and is the second ab-observation mode in which the second a-image and the second b-image are displayed on the display 18 in the automatic switching display aspect in the second a-observation mode or the second b-observation mode.

An eighth pattern 108 shown in FIGS. 24A and 24B comprises two main observation modes and all the main observation modes are specific main observation modes. The specific main observation modes are the first observation mode 81 and the second a-observation mode 82, and comprise the first ab-observation mode 85 as a sub-observation mode for the first observation mode 81 and comprise the second ab-observation mode as a sub-observation mode for the second a-observation mode 82. In FIGS. 24A and 24B, the main observation modes are arranged in the order of the first observation mode 81 and the second a-observation mode 82. However, for example, the second b-observation mode 83 may be provided instead of the second a-observation mode 82.

As described above, the endoscope system 10 has a plurality of observation modes and can flexibly and conveniently perform the switching of the plurality of observation modes including related observation modes by a plurality of operations of a single operation part. Accordingly, it is possible to perform the various type of switching of a plurality of observation modes by, for example, a simple operation, such as pressing, without changing the operation part.

Next, a case where there are a plurality of operation parts will be described. In a case where there are a plurality of operation parts, the first operation and the second operation are assigned to a first operation part and a second operation part that are operation parts different from each other. For example, the first operation part is assigned to the single press operation of the mode changeover switch 12g, and the second operation is assigned to the single press operation of the auxiliary mode changeover switch 12f. In a case where a plurality of operation parts are used, more various types of observation modes can be shifted. Further, for example, a long press operation does not need to be performed.

Figure 25A:
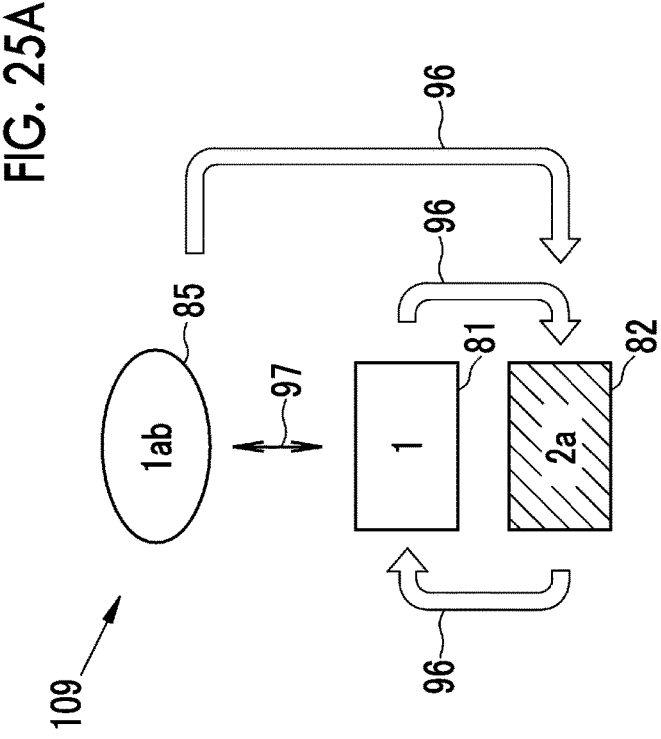
FIG. 25A is a diagram illustrating a ninth pattern of the flow of an observation mode and FIG. 25B is a diagram illustrating a relationship between an operation in the ninth pattern and the observation mode.
Figure 25B:
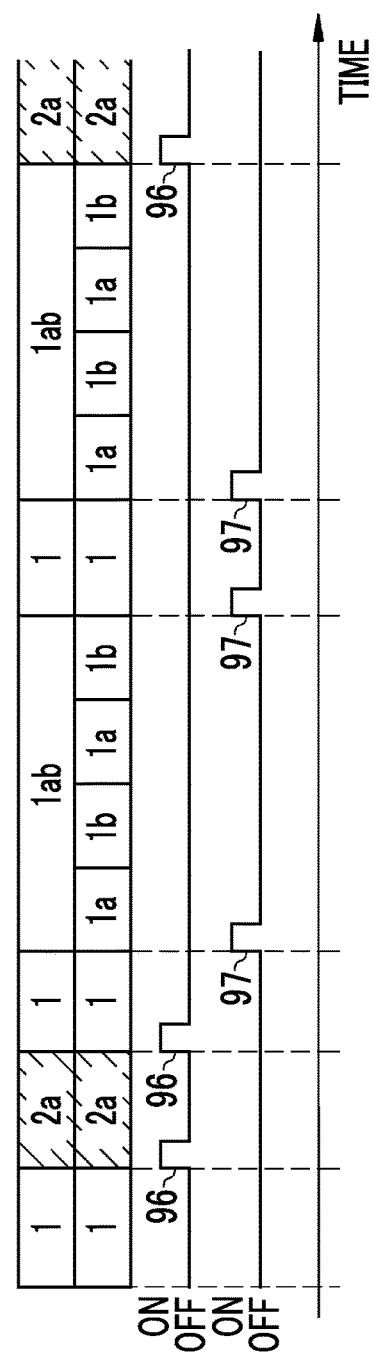

A ninth pattern 109 shown in FIGS. 25A and 25B comprises two main observation modes, and a specific main observation mode is the first observation mode 81 and a sub-observation mode is the first ab-observation mode 85. The endoscope system 10 of the ninth pattern 109 uses the mode changeover switch 12g and the auxiliary mode changeover switch 12f as the first operation part and the second operation part, respectively, and determines that an operation is performed by the press of the switch without determining whether an operation is a single press operation or a long press operation. In a case where a first pressing operation 96 for pressing the mode changeover switch 12g is set as the first operation and a second pressing operation 97 for pressing the auxiliary mode changeover switch 12f is set as the second operation, the first pressing operation 96 is performed to perform the main switching processing. Accordingly, the first observation mode 81 and the second a-observation mode 82 are switched. Then, in a case where the second pressing operation 97 is performed during an observation made in the first observation mode 81 that is a specific main observation mode, sub-switching processing is performed. Accordingly, the first observation mode 81 and the first ab-observation mode 85 are switched to each other.

As shown in FIGS. 25A and 25B, in a case where the first pressing operation 96 is performed even during an observation made in the first ab-observation mode 85, the first ab-observation mode 85 is shifted to the second a-observation mode 82 that is the next main observation mode. Accordingly, in this case, the first pressing operation 96 allows main shift processing for switching a sub-observation mode to the next main observation mode to be also performed in addition to the main switching processing for switching the plurality of main observation modes in a predetermined order. Therefore, in the ninth pattern 109, there are a plurality of methods of shifting an observation mode to the second a-observation mode 82 that is the main observation mode, one method is a method of shifting the first observation mode 81, which is a specific main observation mode, by the first pressing operation 96, and the other method is a method of shifting the first ab-observation mode 85, which is a sub-observation mode, by the second pressing operation 97.

Figure 26:
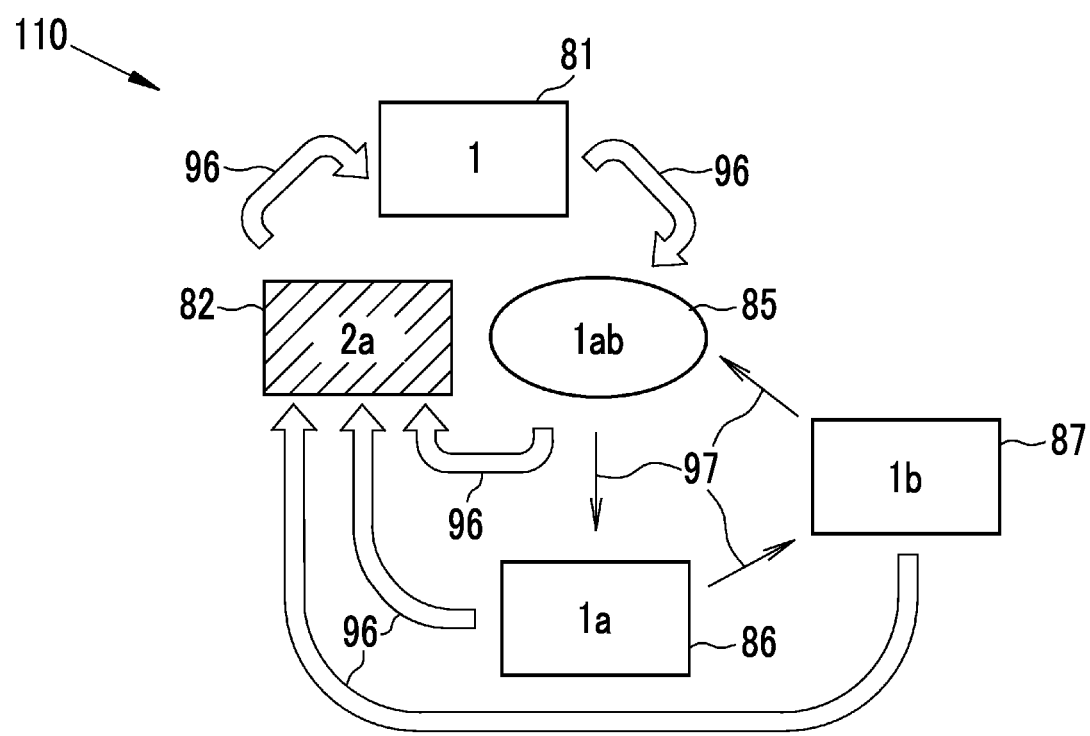
FIG. 26 is a diagram illustrating a tenth pattern of the flow of an observation mode.
Figure 27:
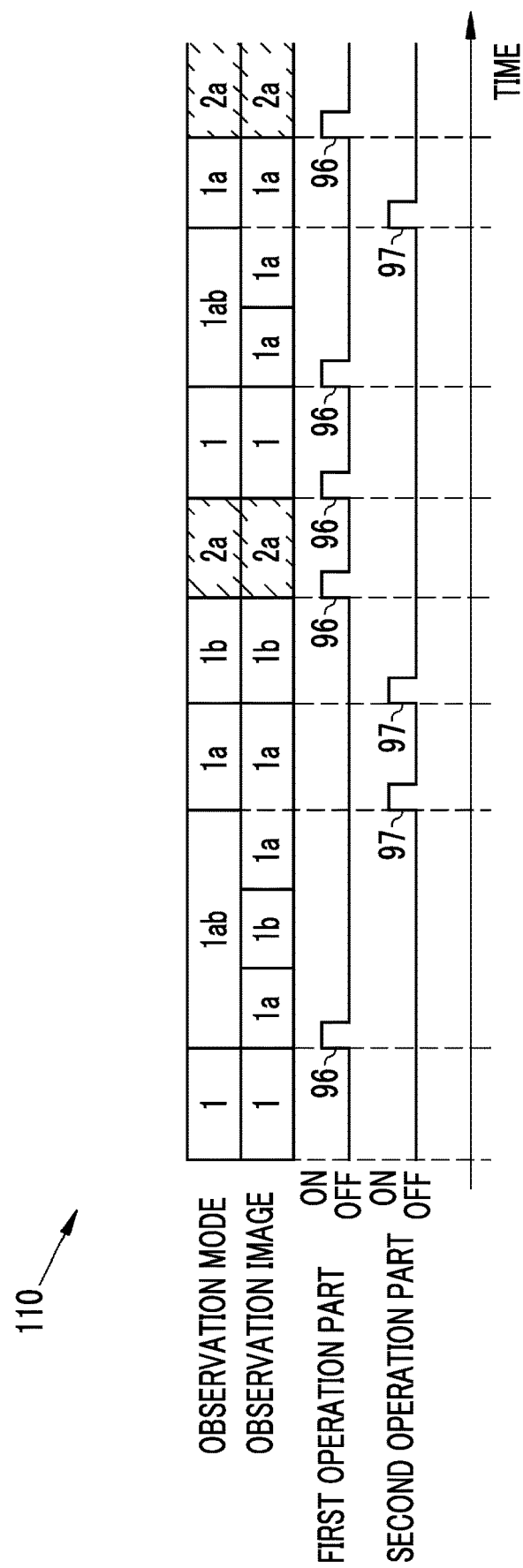
FIG. 27 is a diagram illustrating a relationship between an operation in the tenth pattern and the observation mode.

A tenth pattern 110 shown in FIGS. 26 and 27 is a pattern in a case where there are a plurality of sub-observation modes. The tenth pattern 110 comprises three main observation modes, that is, the first observation mode 81, the first ab-observation mode 85, and the second a-observation mode 82, and a specific main observation mode is the first ab-observation mode 85 and comprises two modes, that is, the first a-observation mode 86 and the first b-observation mode 87 as sub-observation modes. The second b-observation mode 83 may be provided instead of the second a-observation mode 82.

The first pressing operation 96 for pressing the mode changeover switch 12g is set as the first operation and the second pressing operation 97 for pressing the auxiliary mode changeover switch 12f is set as the second operation. In a case where the first pressing operation 96 is performed, the main switching processing is performed. Accordingly, the first observation mode 81, the first ab-observation mode 85, and the second a-observation mode 82 are switched in this order. In a case where the second pressing operation 97 is performed during an observation made in the first ab-observation mode 85, which is a specific main observation mode, the sub-switching processing is performed. The first ab-observation mode 85, which is a specific main observation mode, includes two observation modes, that is, the first a-observation mode 86 and the first b-observation mode 87 as sub-observation modes. Accordingly, with regard to the sub-switching processing, the first ab-observation mode 85 is switched to the first a-observation mode 86, which is one of the sub-observation modes, in a case where the second pressing operation 97 is performed during an observation made in the first ab-observation mode 85, the first a-observation mode 86 is switched to the first b-observation mode 87 in a case where the second pressing operation 97 is performed during an observation made in the first a-observation mode 86, and the first b-observation mode 87 is switched to the first ab-observation mode 85 in a case where the second pressing operation 97 is performed during an observation made in the first b-observation mode 87.

Further, in the tenth pattern 110, as in the ninth pattern 109, the first pressing operation 96 allows main shift processing for switching a sub-observation mode to the next main observation mode to be also performed in addition to the main switching processing for switching a plurality of main observation modes in a predetermined order. Accordingly, as shown in FIGS. 26 and 27, in a case where the first pressing operation 96 is performed during an observation made in the first a-observation mode 86 or the first b-observation mode 87 that is a sub-observation mode, the first a-observation mode 86 or the first b-observation mode 87 is shifted to the second a-observation mode 82 that is the next main observation mode.

Figure 28:
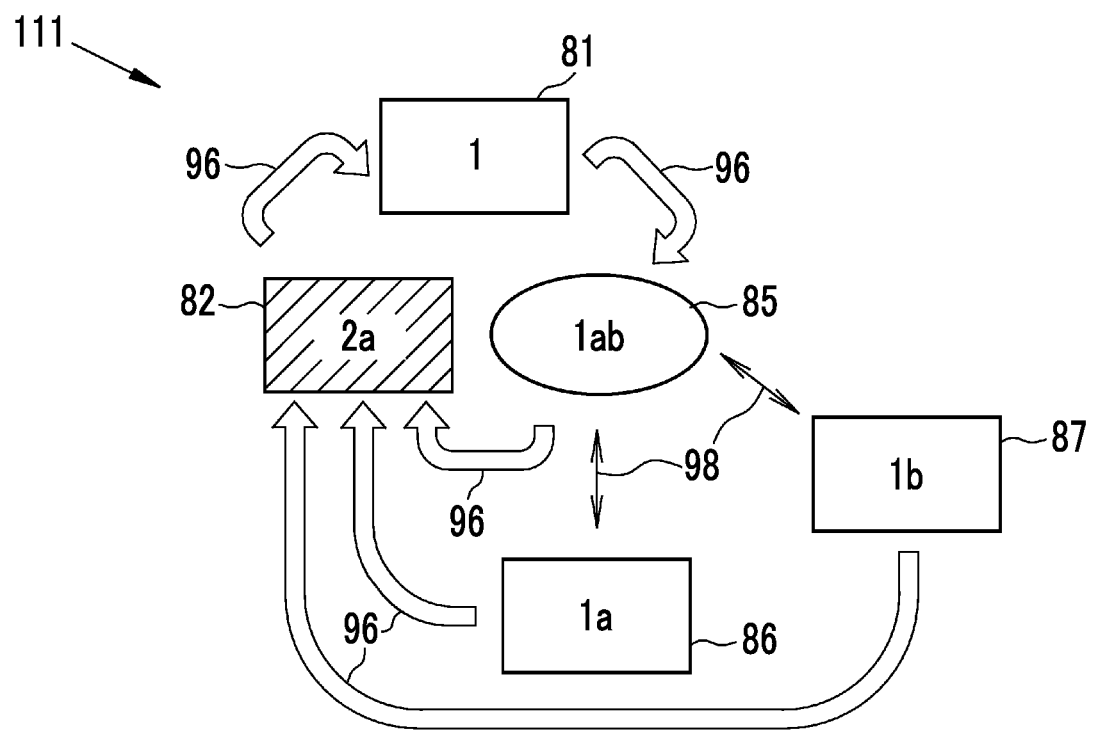
FIG. 28 is a diagram illustrating an eleventh pattern of the flow of an observation mode.
Figure 29:
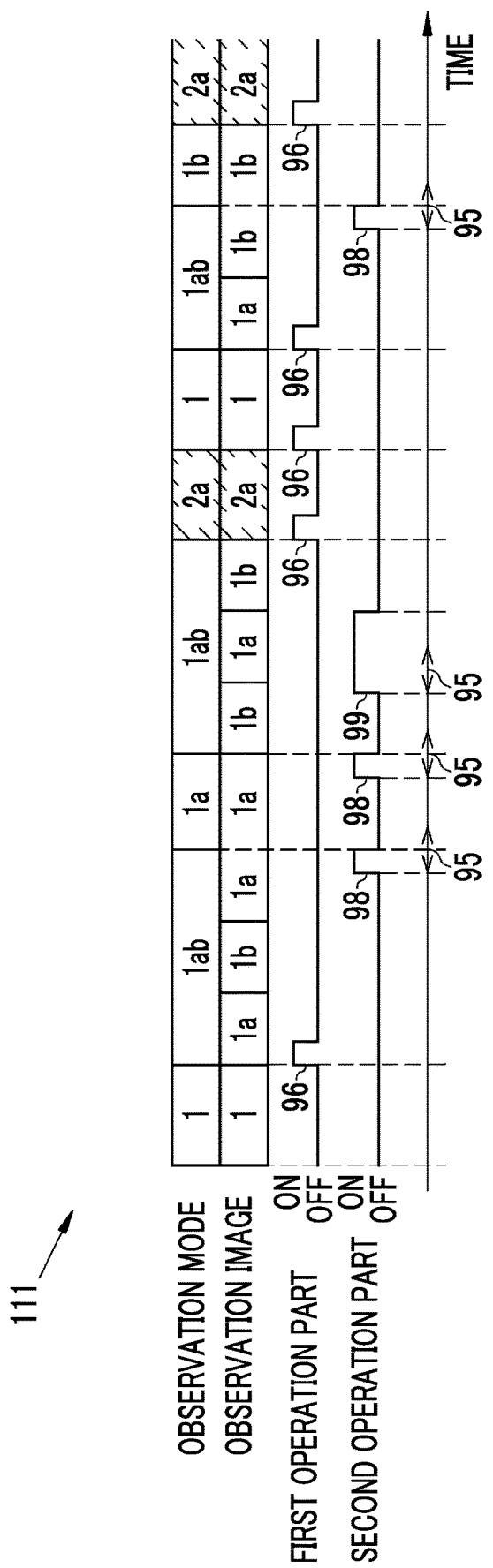
FIG. 29 is a diagram illustrating a relationship between an operation in the eleventh pattern and the observation mode.

An eleventh pattern 111 shown in FIGS. 28 and 29 is a pattern in a case where a first operation part and a second operation part are provided and at least one operation part of the first operation part or the second operation part includes a long press operation. The eleventh pattern 111 comprises three main observation modes, that is, the first observation mode 81, the first ab-observation mode 85, and the second a-observation mode 82, and a specific main observation mode is the first ab-observation mode 85 and comprises two modes, that is, the first a-observation mode 86 and the first b-observation mode 87 as sub-observation modes. The second b-observation mode 83 may be provided instead of the second a-observation mode 82.

The auxiliary mode changeover switch 12f has a pressing operation. The first pressing operation 96 for pressing the mode changeover switch 12g is set as the first operation. The auxiliary mode changeover switch 12f has a single press operation and a long press operation. The determination and the like of a single press operation or a long press operation are the same as described above, a second single press operation 98 for pressing the auxiliary mode changeover switch 12f for a time less than a certain time is set as the second operation, and a second long press operation 99 for pressing the auxiliary mode changeover switch 12f for a time equal to or longer than the certain time is set as a third operation. The third operation allows processing, which is different from the processing of the first and second operations, to be performed.

In a case where the first pressing operation 96 is performed, the main switching processing is performed. Accordingly, the first observation mode 81, the first ab-observation mode 85, and the second a-observation mode 82 are switched in this order. In a case where the second pressing operation 97 is performed during an observation made in the first ab-observation mode 85, which is a specific main observation mode, the sub-switching processing is performed. The first ab-observation mode 85, which is a specific main observation mode, initially includes the first a-observation mode 86 as a sub-observation mode. Accordingly, in a case where the sub-switching processing to be performed by the second pressing operation 97 is repeated, the first ab-observation mode 85 and the first a-observation mode 86 are shifted to each other. However, in a case where the second long press operation 99 is performed during an observation made in the first ab-observation mode 85 that is a specific main observation mode, a sub-observation mode combined with the first ab-observation mode 85, which is a specific main observation mode, is changed to the first b-observation mode 87 from the first a-observation mode 86. After that, the sub-switching processing to be performed by the second pressing operation 97 is shifted between the first ab-observation mode 85 and the first b-observation mode 87.

Further, as in the ninth pattern 109 and the tenth pattern 110, the first pressing operation 96 allows main shift processing for switching a sub-observation mode to the next main observation mode to be also performed in addition to the main switching processing for switching a plurality of main observation modes in a predetermined order. Accordingly, as shown in FIGS. 28 and 29, in a case where the first pressing operation 96 is performed during an observation made in the first a-observation mode 86 or the first b-observation mode 87 that is a sub-observation mode, the first a-observation mode 86 or the first b-observation mode 87 is shifted to the second a-observation mode 82 that is the next main observation mode.

As described above, the endoscope system 10 has a plurality of observation modes and can more flexibly and conveniently perform the switching of the plurality of observation modes including related observation modes by a plurality of operation parts. In particular, since a plurality of operations, such as a single press operation and a long press operation, can be set to the plurality of operation parts, the switching of the plurality of observation mode can be performed in more various patterns.

The hardware structures of the processing units, which are included in the processor device 16 in the embodiment, such as the image acquisition unit 52, the DSP 54, the noise removing unit 57, the central controller 58, the image processing unit 61, and the display controller 65, are various processors to be described below. The various processors include: a central processing unit (CPU) that is a general-purpose processor functioning as various processing units by executing software (program); a programmable logic device (PLD) that is a processor of which the circuit configuration can be changed after manufacture, such as a field programmable gate array (FPGA); a dedicated electrical circuit that is a processor having circuit configuration designed exclusively to perform various types of processing; and the like.

One processing unit may be formed of one of these various processors, or may be formed of a combination of two or more same type or different types of processors (for example, a plurality of FPGAs, or a combination of a CPU and an FPGA). Further, a plurality of processing units may be formed of one processor. As an example where a plurality of processing units are formed of one processor, first, there is an aspect in which one processor is formed of a combination of one or more CPUs and software as typified by a computer, such as a client or a server, and functions as a plurality of processing units. Second, there is an aspect in which a processor fulfilling the functions of the entire system, which includes a plurality of processing units, by one integrated circuit (IC) chip as typified by System On Chip (SoC) or the like is used. In this way, various processing units are formed of one or more of the above-mentioned various processors as hardware structures.

In addition, the hardware structures of these various processors are more specifically electrical circuitry where circuit elements, such as semiconductor elements, are combined.

The present invention can also be embodied by another embodiment to be described below.

A processor device of an endoscope system
displays an observation image on a display in a specific display aspect in each observation mode in a case where the processor has a plurality of observation modes including a plurality of main observation modes and a sub-observation mode, and
performs main switching processing for switching the plurality of main observation modes in a predetermined order according to a first operation and performs sub-switching processing for performing switching between a specific main observation mode of the plurality of main observation modes and the sub-observation mode according to a second operation different from the first operation,
wherein the specific display aspect includes an automatic switching display aspect in which a plurality of the observation images are automatically switched and displayed on the display and a continuous display aspect in which the observation image is continuously displayed on the display, and
the observation image displayed in the specific main observation mode and the observation image displayed in the sub-observation mode have the same base color tone.

EXPLANATION OF REFERENCES

10: endoscope system
12: endoscope
12a: insertion part
12b: operation part
12c: bendable part
12d: distal end part
12e: angle knob
12f: auxiliary mode changeover switch
12g: mode changeover switch
12h: zoom operation part
14: light source device
16: processor device
18: display
19: console
20: light source unit
20a: V-LED
20b: B-LED
20c: G-LED
20d: R-LED
22: light source controller
24: optical path-combination unit
26: light emission period-setting unit
30a: illumination optical system
30b: image pickup optical system
41: light guide
45: illumination lens
46: objective lens
48: image pickup sensor
48b: B filter
48g: G filter
48r: R filter
50: CDS/AGC circuit
51: A/D converter
52: image acquisition unit
54: DSP
57: noise removing unit
58: central controller
59: mode switching controller
61: image processing unit
65: display controller
66: observation mode setting section
67: operation recognition section
69: instruction section
71: emission of illumination light
73: frame
75: first period
76: second period
77: third period
78: fourth period
81: first observation mode
82: second a-observation mode
83: second b-observation mode
84: second ab-observation mode
85: first ab-observation mode
86: first a-observation mode
87: first b-observation mode
91: single press operation
92: long press operation 93: long press release operation
95: long press determination time
96: first pressing operation
97: second pressing operation
98: second single press operation
99: second long press operation
101: first pattern
102: second pattern
103: third pattern
104: fourth pattern
105: fifth pattern
106: sixth pattern
107: seventh pattern
108: eighth pattern
109: ninth pattern
110: tenth pattern
111: eleventh pattern

What is claimed is:

1. An endoscope system comprising:
a processor configured to:
display an observation image on a display in a specific display aspect in each observation mode in a case where the processor has a plurality of observation modes including a plurality of main observation modes and a sub-observation mode; and
perform main switching processing for switching the plurality of main observation modes in a predetermined order according to a first operation and performs sub-switching processing for performing switching between a specific main observation mode of the plurality of main observation modes and the sub-observation mode according to a second operation different from the first operation, wherein
the specific display aspect includes an automatic switching display aspect in which a plurality of the observation images are automatically switched and displayed on the display and a continuous display aspect in which the observation image is continuously displayed on the display,
the observation image displayed in the specific main observation mode and the observation image displayed in the sub-observation mode have the same base color tone,
the observation images are displayed on the display in the automatic switching display aspect in the specific main observation mode,
the observation image is displayed on the display in the continuous display aspect in the sub-observation mode,
the specific main observation mode is a first ab-observation mode in which two images, that is, a first a-image and a first b-image having a first base color tone are displayed on the display in the automatic switching display aspect, and
the sub-observation mode is any one of a first a-observation mode in which the first a-image having the first base color tone is displayed on the display in the continuous display aspect or a first b-observation mode in which the first b-image having the first base color tone is displayed on the display in the continuous display aspect.

2. An endoscope system comprising:
a processor configured to:
display an observation image on a display in a specific display aspect in each observation mode in a case where the processor has a plurality of observation modes including a plurality of main observation modes and a sub-observation mode; and
perform main switching processing for switching the plurality of main observation modes in a predetermined order according to a first operation and performs sub-switching processing for performing switching between a specific main observation mode of the plurality of main observation modes and the sub-observation mode according to a second operation different from the first operation, wherein
the specific display aspect includes an automatic switching display aspect in which a plurality of the observation images are automatically switched and displayed on the display and a continuous display aspect in which the observation image is continuously displayed on the display, and
the observation image displayed in the specific main observation mode and the observation image displayed in the sub-observation mode have the same base color tone,
the observation image is displayed on the display in the continuous display aspect in the specific main observation mode,
the observation images are displayed on the display in the automatic switching display aspect in the sub-observation mode,
the specific main observation mode is any one of a first a-observation mode in which a first a-image having a first base color tone is displayed on the display in the continuous display aspect or a first b-observation mode in which a first b-image having the first base color tone is displayed on the display in the continuous display aspect, and
the sub-observation mode is a first ab-observation mode in which two images, that is, the first a-image and the first b-image having the first base color tone are displayed on the display in the automatic switching display aspect.

3. An endoscope system comprising:
a processor configured to:
display an observation image on a display in a specific display aspect in each observation mode in a case where the processor has a plurality of observation modes including a plurality of main observation modes and a sub-observation mode; and
perform main switching processing for switching the plurality of main observation modes in a predetermined order according to a first operation and performs sub-switching processing for performing switching between a specific main observation mode of the plurality of main observation modes and the sub-observation mode according to a second operation different from the first operation, wherein
the specific display aspect includes an automatic switching display aspect in which a plurality of the observation images are automatically switched and displayed on the display and a continuous display aspect in which the observation image is continuously displayed on the display,
the observation image displayed in the specific main observation mode and the observation image displayed in the sub-observation mode have the same base color tone,
the observation image is displayed on the display in the continuous display aspect in the specific main observation mode,
the observation images are displayed on the display in the automatic switching display aspect in the sub-observation mode, the specific main observation mode is a first observation mode in which a first image having a first base color tone is displayed on the display in the continuous display aspect, and the sub-observation mode is a first ab-observation mode in which two images, that is, a first a-image and a first b-image having the first base color tone are displayed on the display in the automatic switching display aspect.

4. The endoscope system according to claim 1, wherein a plurality of the specific main observation modes are provided.

5. The endoscope system according to claim 4, wherein the specific main observation mode includes at least one specific main observation mode in which an image having a first base color tone is displayed on the display and at least one specific main observation mode in which an image having a second base color tone is displayed on the display.

6. The endoscope system according to claim 1, further comprising:
a specific operation part that is used to perform both the first operation and the second operation.

7. The endoscope system according to claim 6, wherein the first operation is a single press operation for pressing the specific operation part for a time less than a certain time and the second operation is a long press operation for pressing the specific operation part for a time equal to or longer than the certain time or a long press release operation for releasing the pressing of the specific operation part.

8. The endoscope system according to claim 1, further comprising:
a first operation part that is used to perform the first operation; and
a second operation part that is used to perform the second operation.

* * * * *